US008916554B2

(12) United States Patent
Angibaud et al.

(10) Patent No.: US 8,916,554 B2
(45) Date of Patent: Dec. 23, 2014

(54) AMINO-DERIVATIVES AS NOVEL INHIBITORS OF HISTONE DEACETYLASE

(71) Applicant: Janssen Pharmaceutica N.V., Beerse (BE)

(72) Inventors: Patrick René Angibaud, Fontaine-Bellinger (FR); Kristof Van Emelen, Sint-Niklaas (BE); Virginie Sophie Poncelet, Le Manoir sur Seine (FR); Bruno Roux, Saint Leger du Bourg-Denis (FR)

(73) Assignee: Janssen Pharmaceutica, N.V., Beerse (BE)

( * ) Notice: Subject to any disclaimer, the term of this patent is extended or adjusted under 35 U.S.C. 154(b) by 0 days.

(21) Appl. No.: 13/947,308

(22) Filed: Jul. 22, 2013

(65) Prior Publication Data

US 2013/0303506 A1    Nov. 14, 2013

Related U.S. Application Data

(62) Division of application No. 13/471,579, filed on May 15, 2012, now Pat. No. 8,524,711, which is a division of application No. 12/429,838, filed on Apr. 24, 2009, now abandoned, which is a division of application No. 10/507,784, filed as application No. PCT/EP03/02513 on Mar. 11, 2003, now Pat. No. 7,541,369.

(60) Provisional application No. 60/363,799, filed on Mar. 13, 2002.

(51) Int. Cl.
*A61K 31/506* (2006.01)
*C07D 401/12* (2006.01)
*C07D 401/14* (2006.01)
*A61K 31/454* (2006.01)
*A61K 31/55* (2006.01)
(Continued)

(52) U.S. Cl.
CPC ............... *A61K 31/40* (2013.01); *A61K 31/454* (2013.01); *A61K 31/55* (2013.01); *C12Q 1/48* (2013.01); *C07D 217/16* (2013.01); *C07D 307/68* (2013.01); *C07D 239/42* (2013.01); *A61K 45/06* (2013.01); *C07D 295/26* (2013.01); *A61K 31/495* (2013.01); *A61K 31/506* (2013.01); *C07D 471/04* (2013.01); *C07D 401/04* (2013.01); *C07D 401/12* (2013.01); *A61K 31/472* (2013.01); *C07D 295/155* (2013.01); *A61K 31/496* (2013.01); *C07D 409/12* (2013.01); *C07D 207/09* (2013.01); *C07D 513/04* (2013.01); *A61K 31/5377* (2013.01); *C07D 403/04* (2013.01); *C07D 211/58* (2013.01); *C07D 405/06* (2013.01); *C07D 207/14* (2013.01); *C07D 213/78* (2013.01); *A61K 31/435* (2013.01);

*C07D 217/02* (2013.01); *C07D 413/04* (2013.01); *C07D 471/10* (2013.01); *A61K 31/4427* (2013.01)
USPC ................... 514/235.8; 514/217.05; 514/248; 514/252.18; 514/260.1; 514/262.1; 514/266.2; 514/275; 540/599; 540/600; 540/601; 544/122; 544/235; 544/262; 544/278; 544/284; 544/295; 544/296; 544/323; 544/324; 544/325; 544/331; 544/332

(58) Field of Classification Search
USPC ........... 514/235.8, 248, 252.18, 260.1, 262.1, 514/266.2, 275; 544/122, 235, 262, 278, 544/284, 295, 296, 323, 324, 325, 331, 332
See application file for complete search history.

(56) References Cited

U.S. PATENT DOCUMENTS 3,331,843 A    7/1967    Tomcufcik et al.
3,459,731 A    8/1969    Gramera et al.
(Continued)

FOREIGN PATENT DOCUMENTS

CA    2491131    1/2004
CA    2518950    2/2005
(Continued)

OTHER PUBLICATIONS

Acharya et al., "Rational Development of Histone Deacetylase Inhibitors as Anticancer Agents: A Review," Molecular Pharmacology, 2005, 68(4), 917-932.
(Continued)

*Primary Examiner* — Brenda Coleman
(74) *Attorney, Agent, or Firm* — Baker & Hostetler LLP

(57) ABSTRACT

This invention comprises the novel compounds of formula (I)

(I)

wherein n, m, t, $R^1$, $R^2$, L, Q, X, Y, Z and

—$\bigcirc$— have defined meanings, having histone deacetylase inhibiting enzymatic activity; their preparation, compositions containing them and their use as a medicine.

11 Claims, No Drawings

(51) Int. Cl.

| | |
|---|---|
| C12Q 1/48 | (2006.01) |
| C07D 217/16 | (2006.01) |
| C07D 307/68 | (2006.01) |
| C07D 239/42 | (2006.01) |
| A61K 45/06 | (2006.01) |
| C07D 295/26 | (2006.01) |
| A61K 31/495 | (2006.01) |
| C07D 471/04 | (2006.01) |
| C07D 401/04 | (2006.01) |
| A61K 31/472 | (2006.01) |
| C07D 295/155 | (2006.01) |
| A61K 31/496 | (2006.01) |
| C07D 409/12 | (2006.01) |
| C07D 207/09 | (2006.01) |
| C07D 513/04 | (2006.01) |
| A61K 31/5377 | (2006.01) |
| C07D 403/04 | (2006.01) |
| C07D 211/58 | (2006.01) |
| C07D 405/06 | (2006.01) |
| C07D 207/14 | (2006.01) |
| C07D 213/78 | (2006.01) |
| A61K 31/435 | (2006.01) |
| A61K 31/40 | (2006.01) |
| C07D 217/02 | (2006.01) |
| C07D 413/04 | (2006.01) |
| C07D 471/10 | (2006.01) |
| A61K 31/4427 | (2006.01) |

(56) References Cited

U.S. PATENT DOCUMENTS

| | | | |
|---|---|---|---|
| 3,966,743 A | 6/1976 | Berger et al. | |
| 4,049,811 A | 9/1977 | Berger et al. | |
| 4,348,401 A | 9/1982 | Friebe et al. | |
| 4,455,422 A | 6/1984 | Banno et al. | |
| 5,025,012 A | 6/1991 | Miura et al. | |
| 5,147,876 A | 9/1992 | Mizuchi et al. | |
| 5,338,738 A | 8/1994 | Matson et al. | |
| 5,342,846 A | 8/1994 | Singh et al. | |
| 5,780,454 A | 7/1998 | Adams et al. | |
| 5,789,412 A | 8/1998 | Halazy et al. | |
| 5,952,349 A * | 9/1999 | Asberom et al. | 514/316 |
| 6,066,730 A | 5/2000 | Adams et al. | |
| 6,083,903 A | 7/2000 | Adams et al. | |
| 6,294,538 B1 | 9/2001 | Mylari | |
| 6,518,283 B1 | 2/2003 | Langham et al. | |
| 6,589,950 B1 | 7/2003 | Collingwood et al. | |
| 6,897,307 B2 | 5/2005 | Ciszewski et al. | |
| 7,205,304 B2 | 4/2007 | Van Emelen et al. | |
| 7,446,109 B2 | 11/2008 | Van Emelen et al. | |
| 7,501,417 B2 | 3/2009 | Van Emelen et al. | |
| 7,541,369 B2 | 6/2009 | Angibaud et al. | |
| 7,592,450 B2 | 9/2009 | Van Emelen | |
| 7,615,553 B2 | 11/2009 | Van Emelen et al. | |
| 7,704,998 B2 | 4/2010 | Van Emelen et al. | |
| 7,709,487 B2 | 5/2010 | Van Emelen et al. | |
| 7,767,679 B2 | 8/2010 | Van Emelen et al. | |
| 7,816,363 B2 | 10/2010 | Angibaud et al. | |
| 7,834,011 B2 | 11/2010 | Roux et al. | |
| 7,834,025 B2 | 11/2010 | Angibaud et al. | |
| 7,884,105 B2 | 2/2011 | Van Emelen | |
| 7,888,360 B2 | 2/2011 | Angibaud et al. | |
| 7,947,830 B2 | 5/2011 | Van Brandt et al. | |
| 8,071,615 B2 | 12/2011 | Van Emelen et al. | |
| 8,097,611 B2 | 1/2012 | Van Emelen et al. | |
| 8,101,616 B2 | 1/2012 | Angibaud et al. | |
| 8,114,876 B2 | 2/2012 | Marconnet-Decrane et al. | |
| 8,114,999 B2 | 2/2012 | Van Emelen et al. | |
| 8,119,650 B2 | 2/2012 | Angibaud et al. | |
| 8,138,198 B2 | 3/2012 | Angibaud et al. | |
| 8,163,519 B2 | 4/2012 | Ko et al. | |

| | | | |
|---|---|---|---|
| 2002/0032195 A1 | 3/2002 | Breitfelder et al. | |
| 2004/0248897 A1 | 12/2004 | Priepke et al. | |
| 2005/0080258 A1 | 4/2005 | Davis et al. | |
| 2005/0096468 A1 | 5/2005 | Van Emelen et al. | |
| 2005/0107384 A1 | 5/2005 | Angibaud et al. | |
| 2005/0171347 A1 | 8/2005 | Van Emelen et al. | |
| 2005/0197336 A1 | 9/2005 | Anandan et al. | |
| 2005/0222414 A1 | 10/2005 | Van Emelen et al. | |
| 2007/0135424 A1 | 6/2007 | Van Brandt et al. | |
| 2008/0132459 A1 | 6/2008 | Moradei et al. | |
| 2008/0255140 A1 | 10/2008 | Van Emelen | |
| 2009/0005393 A1 | 1/2009 | Angibaud et al. | |
| 2009/0018152 A1 | 1/2009 | Angibaud et al. | |
| 2009/0018153 A1 | 1/2009 | Angibaud et al. | |
| 2009/0023726 A1 | 1/2009 | Roux et al. | |
| 2009/0036463 A1 | 2/2009 | Angibaud et al. | |
| 2009/0042920 A1 | 2/2009 | Van Emelen et al. | |
| 2009/0124646 A1 | 5/2009 | Verdonck et al. | |
| 2009/0143401 A1 | 6/2009 | Marconnet-Decrane et al. | |
| 2009/0170836 A1 | 7/2009 | Angibaud et al. | |
| 2009/0170881 A1 | 7/2009 | Angibaud et al. | |
| 2009/0221580 A1 | 9/2009 | Angibaud et al. | |
| 2009/0227558 A1 | 9/2009 | Angibaud et al. | |
| 2009/0270419 A1 | 10/2009 | Arts et al. | |
| 2010/0009988 A1 | 1/2010 | Van Emelen | |
| 2010/0010004 A1 | 1/2010 | Van Emelen et al. | |
| 2010/0048588 A1 | 2/2010 | Van Emelen et al. | |
| 2010/0160321 A1 | 6/2010 | Ten Holte et al. | |
| 2010/0222574 A1 | 9/2010 | Rombouts et al. | |
| 2010/0234353 A1 | 9/2010 | Van Emelen et al. | |
| 2010/0240639 A1 | 9/2010 | Van Emelen et al. | |

FOREIGN PATENT DOCUMENTS

| | | |
|---|---|---|
| DE | 4228792 | 3/1994 |
| DE | 10233412 | 2/2004 |
| EP | 0076530 | 12/1985 |
| EP | 0188094 | 3/1992 |
| EP | 0827742 | 3/1998 |
| EP | 1002795 | 5/2000 |
| EP | 0788360 | 5/2003 |
| EP | 1472216 | 11/2004 |
| EP | 1485353 | 12/2004 |
| EP | 1495002 | 1/2005 |
| EP | 1523470 | 4/2005 |
| EP | 1525199 | 4/2005 |
| EP | 1572626 | 9/2005 |
| EP | 1583736 | 10/2005 |
| EP | 1585735 | 10/2005 |
| EP | 1592667 | 11/2005 |
| EP | 1312609 | 12/2005 |
| EP | 1608628 | 12/2005 |
| EP | 1613622 | 1/2006 |
| EP | 1663953 | 6/2006 |
| EP | 1501508 | 2/2007 |
| EP | 1581484 | 7/2007 |
| EP | 1592665 | 7/2007 |
| EP | 1685094 | 8/2007 |
| EP | 1485354 | 5/2008 |
| EP | 1485365 | 5/2008 |
| EP | 1485348 | 6/2008 |
| EP | 1485378 | 6/2008 |
| EP | 1492534 | 6/2008 |
| EP | 1627880 | 10/2008 |
| EP | 1485364 | 3/2009 |
| EP | 1485370 | 3/2009 |
| EP | 1682538 | 5/2009 |
| EP | 1611088 | 6/2009 |
| EP | 1590340 | 4/2010 |
| EP | 1673349 | 6/2010 |
| EP | 1485099 | 7/2010 |
| ES | 2104509 | 10/1997 |
| GB | 901749 | 7/1962 |
| GB | 1345872 | 2/1974 |
| WO | WO 94/25437 | 11/1994 |
| WO | WO 96/13266 | 5/1996 |
| WO | WO 97/18839 | 5/1997 |
| WO | WO 97/23216 | 7/1997 |
| WO | WO 98/05335 | 2/1998 |

(56) References Cited

FOREIGN PATENT DOCUMENTS

| | | |
|---|---|---|
| WO | WO 98/55449 | 12/1998 |
| WO | WO 99/50250 | 10/1999 |
| WO | WO 00/26203 | 5/2000 |
| WO | WO 00/27825 | 5/2000 |
| WO | WO 00/35855 | 6/2000 |
| WO | WO 0043394 | 7/2000 |
| WO | WO 00/52001 | 9/2000 |
| WO | WO 00/71516 | 11/2000 |
| WO | WO 01/09134 | 2/2001 |
| WO | WO 01/38322 | 5/2001 |
| WO | WO 01/49688 | 7/2001 |
| WO | WO 01/70675 | 9/2001 |
| WO | WO 02/00651 | 1/2002 |
| WO | WO 02/18335 | 3/2002 |
| WO | WO 02/42271 | 5/2002 |
| WO | WO 03/000653 | 1/2003 |
| WO | WO 03/011851 | 2/2003 |
| WO | WO 03/016306 | 2/2003 |
| WO | WO 03/035855 | 5/2003 |
| WO | WO 03/066579 | 8/2003 |
| WO | WO 03/075929 | 9/2003 |
| WO | WO 03/076395 | 9/2003 |
| WO | WO 03/076400 | 9/2003 |
| WO | WO 03/076401 | 9/2003 |
| WO | WO 03/076421 | 9/2003 |
| WO | WO 03/076422 | 9/2003 |
| WO | WO 03/076438 | 9/2003 |
| WO | WO 03/082288 | 10/2003 |
| WO | WO 03/087057 | 10/2003 |
| WO | WO 03/092686 | 11/2003 |
| WO | WO 2004/009536 | 1/2004 |
| WO | WO 2004/013130 | 2/2004 |
| WO | WO 2004/056748 | 7/2004 |
| WO | WO 2004/063146 | 7/2004 |
| WO | WO 2004/063169 | 7/2004 |
| WO | WO 2004/065354 | 8/2004 |
| WO | WO 2004/069803 | 8/2004 |
| WO | WO 2004/069823 | 8/2004 |
| WO | WO 2004/071400 | 8/2004 |
| WO | WO 2004/072047 | 8/2004 |
| WO | WO 2004/082638 | 9/2004 |
| WO | WO 2004/087693 | 10/2004 |
| WO | WO 2004/092115 | 10/2004 |
| WO | WO 2005/028447 | 3/2005 |
| WO | WO 2005/030704 | 4/2005 |
| WO | WO 2005/030705 | 4/2005 |
| WO | WO 2005/040101 | 5/2005 |
| WO | WO 2005/040161 | 5/2005 |
| WO | WO 2005/075469 | 8/2005 |
| WO | WO 2005/086898 | 9/2005 |
| WO | WO 2005/092899 | 10/2005 |
| WO | WO 2006/010749 | 2/2006 |
| WO | WO 2006/010750 | 2/2006 |
| WO | WO 2006/122926 | 11/2006 |
| WO | WO 2006/136553 | 12/2006 |
| WO | WO 2007/016532 | 2/2007 |
| WO | WO 2007/048767 | 5/2007 |
| WO | WO 2007/082873 | 7/2007 |
| WO | WO 2007/082874 | 7/2007 |
| WO | WO 2007/082876 | 7/2007 |
| WO | WO 2007/082878 | 7/2007 |
| WO | WO 2007/082880 | 7/2007 |
| WO | WO 2007/082882 | 7/2007 |
| WO | WO 2008/031820 | 3/2008 |

OTHER PUBLICATIONS

Angibaud et al., "Discovery of Pyrimidyi-5-Hydroxamic Acids as New Potent Histone Deacetylase Inhibitors," European Journal of Medicinal Chemistry, 2005, 40, 597-606.
Archibald et al., "Benzamidopiperidines 3. Carbocyclic Derivatives Related to Indoramin," Journal of Medicinal Chemistry, 1974 17(7), 739-744.
Awada et al., "The Pipeline of New Anticancer Agents for Breast Cancer Treatment in 2003," Oncology Hematology, 2003, 48, 45-63.
Bali et al., "A Combination of Histone Deacetylase Inhibitor LAQ 824 and the FLT-3 Kinase Inhibitor PKC412 is Highly Active Against Human AML Cells With Constitutively Active Mutant FLT-3 Tyrosine Kinase," Blood, 2003, 102(11), 96a-97b.
Bali et al., "Inhibition of Histone Deacetylase 6 Acetylates and Disrupts the Chaperone Function of Heat Shock Protein 90," Journal of Biological Chemistry, 2005, 280(29), 26729-26734.
Bali et al., "Mechanisms Underlying Hydroxamic Acid Analogue (HA) Histone Deacetylase (HDAC) Inhibitors (HDis) -Induced Apoptosis, New Role of HDAC6 Inhibition, Acetylation and Inhibition of hsp90 and Depletion of Pro-Growth and ProSurvival Oncoproteins," Proceedings of the American Association for Cancer Research Annual Meetings, 2005, 46(#3268), 769-770.
Banker et al., "Prodrugs," Modern pharmaceuticals, *Marcel Dekker, Inc.*, 3rd Ed. 1996, p. 596.
Bertino et al., "Principles of Cancer," *Cecil's Textbook of Medicine*, 2000, 21St Edition, vol. 1, 1060-1074.
Birch et al., "N-Substituted (2, 3-Dihydro-1, 4-benzodioxin-2-yl)methylamine Derivatives as D2 Antagonists/5-HT1A Partial Agonists with Potential as Atypical Antipsychotic Agents," J. Med. Chern., 3199, 42,3342-3355.
Blagosklonny et al., "Histone Deacetylase Inhibits all Induce P21 but Differentially Cause Tubulin Acetylation, Mitotic Arrest, and Cytotoxicity," Molecular Cancer Therapeutics, 2002, 1(11), 937-941.
Calabresi et al., "Section IX Chemotherapy of Neoplastic Diseases-Introduction," Goodmans & Gilman's The Pharmacological Basis of Therapeutics, 10th Ed., 2001, Hardman JG, Limbird LE, and Gilman AG, Eds, McGraw-Hill, New York 2001, 1381-1388 (1381, 1383-1385, 1388 provided).
Carter et al., Chemotherapy of Cancer, Wiley, 2nd Ed., 1981, 362-365.
Catley et al., "Novel Hydroxamic Acid-Derived HDAC Inhibitor LBH589 Potently Activates Intrinsic and Induces Tubulin Hyperacetylation in Multiple Myeloma," Blood, 2005, 106(11), Abstract 1578, p. 435A.
Chen et al., "A Short and General Approach to the Synthesis of Styryllactones: (+)- Goniodiol, its Acetates and 13-Trifluoromethyl Derivative, (+)-7-epi-Goniodiol and (+)-9- DeoxyQoniopypyrone," Synlett, 2002, 8, 1265-1268.
Chou et al., "Chemotherapeutic Synergism, Potentiation and Antagonism," Encyclopedia of Human Biology, 1991, 2, 371-379.
Chou et al., "Computerized Quantitation of Synergism and Antagonism of Taxol, Topotecan, and Cisplatin Against Human Teratocarcinoma Cell Growth: A Rational Approach to Clinical Protocol DesiQn," J. Nat/. Cancer Inst., 1994, 86(20), 1517-1524.
Chou et al., "Quantitative Analysis of Dose-Effect Relationships: The Combined Effects of Multiple Drugs or Enzyme Inhibitors," Adv. Enzyme Regul., 1984, 22, 27-55.
Chou et al., "The Median-Effect Principle and the Combination Index for Quantitation of Synergism and Antagonism," Synergism and Antagonism in Chemotherapy, 1991, 60-103.
Dankwardt et al., "Solid Phase Synthesis of Aryl and Benzylpiperazines and their Applications in Combinatorial Chemistry," Tetrahedron Letters, 1995 36(28), 4923-4926.
Dermer et al., "Another Anniversary for the War on Cancer," Bio/Technology, 1994, 12, 320.
Dorwald, Side Reactions in organic Synthesis, 2005, Wiley, VCH, Weinheim pg. IX of Preface.
Finney, D.J., "Probit Analyses, A Statistical Treatment of the Sigmoid Response Curve," Graded Responses, Cambridge University Press, 1962, 2nd Ed. Chapter 10.
Finnin et al., "Nature", 1999, 401, 188-193.
Foks et al., "Investigations on Pyrazine Derivatives Part II, Synthesis and Tuberculostatic Action of Some 6-Aikylaminopyrazine-2-carboxylic Acids," Dissert. Parm. Pharmacal., 1972, 24, 576-583.
Foks et al., "Studies on Pyrazine Derivatives Part X, Synthesis and Tuberculostatic Activity of some 6-Cyanolamino-6-Imidazolyl- and Triazolypyrazine-2-Carboxylic Acids Derivatives," Pol. J. PharmcoiPharm., 1978, 30, 105-111.
Freshney et al., "Culture of Animal Cells, A Manual of Basic Technique," Alan R Liss, Inc. New York, 1983, 1-6.

(56) References Cited

OTHER PUBLICATIONS

George et al., "Combination of Histone Deacetylase Inhibitor LBH589 and the hsp90 Inhibitor 17-AAG is Highly Active Against Human CML-BC Cells and AML Cells With Activating Mutation of FLT-3," Blood, 2005, 105(4), 1768-1776.
Glaser, "HDAC Inhibitors: Clinical Update and Mechanism-Based Potential," Biochemical Pharmacology, 2007, 74(5), 659-671.
Golub et al., "Molecular Classification of Cancer: Class Discovery and Class Prediction by Gene Expression Monitoring," Science, 1999, 286, 531-537.
Gorrod et al., "Xenobiotica", 1975, 5, 453-462.
Hideshima et al., "Small-Molecule Inhibition of Proteasome and Aggresome Function Induces Synergistic Antitumor Activity in Multiple Myeloma," PNAS, 2005, 102(24), 85678572.
Horton et al., "Bortezomib Interactions with Chemotherapy Agents in Acute Leukemia in Vitro," Cancer Chemotherapy and Pharmacology, 2006, 58(1), 13-23.
Internal Medicine, 4th Edition, Editor-in-Chief Jay Stein, 1994, Chapters 71-72, pp. 699-715.
International Search Report from PCT/EP03/02510 dated May 22, 2003, 2 pages.
International Search Report from PCT/EP03/02511 dated May 22, 2003, 2 pages.
International Search Report from PCT/EP03/02512 dated Jun. 30, 2003, 4 pages.
International Search Report from PCT/EP03/02514 dated Aug. 13, 2003, 4 pages.
International Search Report from PCT/EP03/02515 dated Aug. 18, 2003, 5 pages.
International Search Report from PCT/EP03/02516 dated Aug. 13, 2003, 3 pages.
International Search Report from PCT/EP03/02517 dated May 22, 2003, 2 pages.
International Search Report from PCT/EP05/53611 dated Jan. 17, 2006, 4 pages.
International Search Report from PCT/EP05/53612 dated Jul. 10, 2005, 3 pages.
International Search Report from PCT/EP06/62324 dated Aug. 16, 2006, 4 pages.
International Search Report from PCT/EP06/63351 dated Aug. 11, 2006, 2 pages.
International Search Report from PCT/EP06/67656 dated Feb. 6, 2007, 4 pages.
International Search Report from PCT/EP07/50370 dated Mar. 14, 2007, 3 pages.
International Search Report from PCT/EP07/50371 dated May 8, 2007, 4 pages.
International Search Report from PCT/EP07/50374 dated Mar. 12, 2007, 4 pages.
International Search Report from PCT/EP07/50376 dated Mar. 28, 2007, 2 pages.
International Search Report from PCT/EP07/50379 dated May 8, 2007, 3 pages.
International Search Report from PCT/EP07/50381 dated Apr. 4, 2007, 2 pages.
International Search Report from PCT/EP07/59523 dated Mar. 20, 2008, 6 pages.
International Search Report re: PCT/EP03/02513, dated May 8, 2003.
Irikura et al., "Absorption, Excretion, and Metabolism of 1 (p-aminobenzoyl)-4-(3, 4, 5-trimethoxybenzamido)piperidine (KU-55)," Pharmacometrics, 1973, 7(7), 985-990. (With English-language Abstract).
Khuthier et al., "Studies of Tertiary Amine Oxides, 9.1 Thermal Rearrangement of 1-(4-Substituted-phenyl)piperidine N-Oxides to the Corresponding N-Hydroxlmines," J. Org. Chem., 1987, 52, 1710-1713.
Kristeleit et al., "Histone Modification Enzymes: Novel Targets for Cancer Drugs," Expert Opin. Emerg. Drugs, 204 9(1), 135-154.

Lentzsch et al., "Combination of Proteasome Inhibitor PS 341 with Histone Acetylase Inhibitor (HDAC) PXD 101 Shows Superior Anti-Myeloma Activity and Inhibits OsteoclastoQenesis," Blood Poster Session, 2005, 106(Abstract 2488), p. 1.
Mai et al., Histone Deacetylation in Epigenetics: an Attractive Target for Anticancer Therapy, Medicinal Research Reviews, 2005 25(3), 261-309.
Marks et al., Nature Reviews: Cancer 1, 2001, 194-202.
Mitsiades et al., Transcriptional Signature of Histone Deacetylase Inhibition in Multiple Myeloma: Biological and Clinical Implications, PNAS, 2004, 101(2), 540-545.
Monneret, "Histone Deacetylase Inhibitors," European Journal of Medicinal Chemistry, 2004, 40, 1-13.
Mosmann, Journal of Immunological Methods, 1983, 65, 55-63.
Nawrocki et al., "Aggresome Disruption: A Novel Strategy to Enhance Bortezomib-Induced Apoptosis in Pancreatic Cancer Cells," Cancer Research, 2006, 66(7), 3773-3781.
Pan et al., "Soluble Polymer-Supported Synthesis of Arylpiperazines," Tetrahedron Letters, 1998, 39, 9505-9508.
Pasternak et al., "Potent, orally bioavailable somoatostatin agonists, good absorption achieved by urea backbone cyclization," Bioorganic and Medicinal Chemistry Letters 9, 1992, 9, 491-496.
Patani et al., "Bioisosterism: A Rational Approach in Drug Design," Chem. Rev., 1996, 96, 3147-3176.
Pei Xin-Yan et al., "Synergistic Induction of Oxidative Injury and Apoptosis in Human Multiple Myeloma Cells by the Proteasome Inhibitor Bortezomib and Histone Deacetylase Inhibitors," Clinical Cancer Research, 2004, 10, 3839-3852.
Sausville et al., "Contributions of Human Tumor Xenografts to Anticancer Drug Development," American Association for Cancer Research, 2006, 66(7), 3351-3354.
Simone, "Oncology: Introduction," Cecil's Textbook of Medicine, 1996, 201 Ed., 1, 1004-1010.
Sternson et al., "Synthesis of 7200 Small Molecules Based on a Substructural Analysis of the Histone Deacetylase Inhibitors Trichostatin and Trapoxin," Organic Letters, 2001, 3(26), 4239-4242.
Sutheesophon et al., "Histone Deacetylase Inhibitor Despsipeptides (FK228) Induces Apoptosis in Leukemic Cells by Facilitating Mitochondrial Translocation of Bax, Which is Enhanced by the Proteasome Inhibitor Bortezomib," ACTA Haematologica, 2006, 115, 78-90.
Takai et al., "Human Ovarian Carcinoma Cells: Histone Deacetylase Inhibitors Exhibit Antiproliferative Activity and Potently Induce Apoptosis," American Cancer Society, 2004, 101(12), 2760-2770.
Taylor et al., CAPLUS Abstract 55, 33107 (1961).
Van Emelen et al., "Discovery of a Novel Class of Aromatic Hydroxamic Acids as Potent HDAC Inhibitors," AACR-NCI_Eortc International Conference on Molecular Targets and Cancer Therapeutics, 2003, XP009095813.
Van Emelen et al., "Synthesis, Biological Evaluation and Structure Activity Relationships of a Novel Series of Aromatic Hydroxamic Acids As Potent HDAC Inhibitors," European Journal of Cancer Supp., 2004, 2(8), 40-41[Poster Session 125].
Walsh et al., "Synthesis and Antiallergy Activity of N-[2-(Dimethylamino)ethyl]-4-aryl-1-piperazinecarboxamide Derivatives," J. Med. Chemistry, 1990, 33, 2028-2032.
Wolff, Burgers Medicinal Chemistry, 5th Ed. Part 1, 1995, 975-977.
Yokoyama et al., CAPLUS Abstract 105, 208919 (1986).
Yokoyama et al., CAPLUS Abstract 105, 226622 (1986).
Yu et al., "The Proteasome Inhibitor Bortezomib Interacts Synergistically with Histone Deacetylase Inhibitors to Induce Apoptosis in Bcr/Abl+ Cells Sensitive and Resistant to STI571," Blood, 2003, 102, 3765-3774.
U.S. Appl. No. 10/506,998 Non-Final Office Action dated Jun. 19, 2007, 7 pages.
U.S. Appl. No. 10/506,998 Non-Final Office Action dated Oct. 2, 2008, 5 pages.
U.S. Appl. No. 10/507,084 Non-Final Office Action dated Feb. 25, 2008, 5 pages.
U.S. Appl. No. 10/507,084 Non-Final Office Action dated Jun. 22, 2008, 5 pages.
U.S. Appl. No. 10/507,084 Non-Final Office Action dated Jun. 1, 2007, 7 pages.

(56) References Cited

OTHER PUBLICATIONS

U.S. Appl. No. 10/507,159 Non-Final Office Action dated Jun. 25, 2009, 7 pages.
U.S. Appl. No. 10/507,271 Final Office action dated May 2, 2008, 5 pages.
U.S. Appl. No. 10/507,271 Non-Final Office action dated Jul. 25, 2007, 12 pages.
U.S. Appl. No. 10/507,708 Final Office action dated May 8, 2006, 11 pages.
U.S. Appl. No. 10/507,708 Non-Final Office Action dated Nov. 23, 2005, 15 pages.
U.S. Appl. No. 10/507,784 Non-Final Office action dated Apr. 6, 2007, 13 pages.
U.S. Appl. No. 10/507,784 Non-Final Office Acton dated Feb. 13, 2008, 5 pages.
U.S. Appl. No. 10/507,784 Non-Final Office Action dated Sep. 24, 2007, 5 pages.
U.S. Appl. No. 10/507,785 Non-Final Office action Jul. 19, 2007, 16 pages.
U.S. Appl. No. 10/507,785 Non-Final Office Action dated May 13, 2008, 6 pages.
U.S. Appl. No. 10/507,788 Non-Final Office action dated Oct. 19, 2007, 17 pages.
U.S. Appl. No. 11/572,563 Advisory Action dated Jun. 3, 2011, 2 pages.
U.S. Appl. No. 11/572,563 Final Office Action dated Jul. 9, 2010, 8 pages.
U.S. Appl. No. 11/572,563 Final Office Action dated Mar. 3, 2011, 5 pages.
U.S. Appl. No. 11/572,563 Non-Final Office action dated Sep. 29, 2009, 14 pages.
U.S. Appl. No. 11/626,215 Ex-Parte Quayle Action dated Apr. 2, 2009.
U.S. Appl. No. 11/626,215 Non-Final Office action dated Jul. 9, 2008, 14 pages.
U.S. Appl. No. 11/668,906 Non-Final Office Action dated Feb. 20, 2009, 8 pages.
U.S. Appl. No. 11/914,208 Non-Final Office action dated Mar. 10, 2011, 5 pages.
U.S. Appl. No. 11/914,208 Non-Final Office action dated Oct. 1, 2010, 10 pages.
U.S. Appl. No. 11/917,999 Final Office Action dated Feb. 24, 2011, 15 pages.
U.S. Appl. No. 11/917,999 Non-Final Office Action dated Sep. 15, 2010, 13 pages.
U.S. Appl. No. 11/926,759 Non-Final Office Action dated May 13, 2009, 9 pages.
U.S. Appl. No. 12/090,771 Advisory Action dated Dec. 2, 2009, 3 pages.
U.S. Appl. No. 12/090,771 Final Office Action dated Aug. 24, 2009, 6 pages.
U.S. Appl. No. 12/090,771 Non-Final Office Action dated Dec. 23, 2008, 11 pages.
U.S. Appl. No. 12/160,120 Non-Final Office Action dated Sep. 30, 2009, 13 pages.
U.S. Appl. No. 12/160,124 Non-Final Office Action dated Mar. 25, 2011, 12 pages.
U.S. Appl. No. 12/160,133 Non-Final Office Action dated Sep. 29, 2009, 12 pages.
U.S. Appl. No. 12/160,140 Non-Final Office Action dated Aug. 9, 2010, 6 pages.
U.S. Appl. No. 12/160,140 Non-Final Office Action dated Sep. 30, 2009, 14 pages.
U.S. Appl. No. 12/160,156 Non-Final Office Action dated Sep. 29, 2009, 13 pages.
U.S. Appl. No. 12/160,221 Non-Final Office Action dated Jan. 19, 2010, 7 pages.
U.S. Appl. No. 12/233,977 Non-Final Office Action dated Jun. 3, 2010, 6 pages.
U.S. Appl. No. 12/360,139 Final Office Action dated Mar. 17, 2011, 8 pages.
U.S. Appl. No. 12/360,139 Non-Final Office Action dated Aug. 19, 2010, 22 pages.
U.S. Appl. No. 12/372,785 Non-Final Office Action dated Jul. 11, 2011, 5 pages.
U.S. Appl. No. 12/372,801 Final Office Action dated Nov. 29, 2010, 6 pages.
U.S. Appl. No. 12/372,801 Non-Final Office Action dated Dec. 10, 2009, 7 pages.
U.S. Appl. No. 12/372,801 Non-Final Office Acton dated Jun. 10, 2010, 5 pages.
U.S. Appl. No. 12/539,682 Final Office Action dated Feb. 1, 2011, 11 pages.
U.S. Appl. No. 12/539,682 Non-Final Office Action dated Aug. 17, 2010, 8 pages.
U.S. Appl. No. 12/539,682 Non-Final Office Action dated Sep. 30, 2009, 13 pages.
U.S. Appl. No. 12/759,256 Non-Final Office Action dated Jan. 7, 2011, 7 pages.

\* cited by examiner

AMINO-DERIVATIVES AS NOVEL INHIBITORS OF HISTONE DEACETYLASE

CROSS REFERENCE TO RELATED APPLICATIONS

This application is a divisional of U.S. application Ser. No. 13/471,579, filed May 15, 2012, which is a divisional of U.S. application Ser. No. 12/429, 838, filed Apr. 24, 2009, now abandoned, which is a divisional of U.S. application Ser. No. 10/507,784, now U.S. Pat. No. 7,541,369, filed Sep. 13, 2004, which is the National State Entry of International Application No. PCT/EP2003/02513, filed Mar. 11, 2003, which claims the benefit of U.S. Provisional Application No. 60/363,799, filed Mar. 13, 2002, the entireties of which are incorporated by reference.

This invention concerns compounds having histone deacetylase (HDAC) inhibiting enzymatic activity. It further relates to processes for their preparation, to compositions comprising them, as well as their use, both in vitro and in vivo, to inhibit HDAC and as a medicine, for instance as a medicine to inhibit proliferative conditions, such as cancer and psoriasis.

In all eukaryotic cells, genomic DNA in chromatine associates with histones to form nucleosomes. Each nucleosome consists of a protein octamer made up of two copies of each histones H2A, H2B, H3 and H4. DNA winds around this protein core, with the basic amino acids of the histones interacting with the negatively charged phosphate groups of the DNA. The most common posttranslational modification of these core histones is the reversible acetylation of the ε-amino groups of conserved, highly basic N-terminal lysine residues. The steady state of histone acetylation is established by the dynamic equilibrium between competing histone acetyltransferase(s) and histone deacetylase(s) herein referred to as "HDAC". Histone acetylation and deacetylation has long been linked to transcriptional control. The recent cloning of the genes encoding different histone acetyltransferases and histone deacetylases provided a possible explanation for the relationship between histone acetylation and transcriptional control. The reversible acetylation of histones can result in chromatin remodelling and as such act as a control mechanism for gene transcription. In general, hyperacetylation of histones facilitates gene expression, whereas histone deacetylation is correlated with transcriptional repression. Histone acetyltransferases were shown to act as transcriptional coactivators, whereas histone deacetylases were found to belong to transcriptional repression pathways.

The dynamic equilibrium between histone acetylation and deacetylation is essential for normal cell growth. Inhibition of histone deacetylase results in cell cycle arrest, cellular differentiation, apoptosis and reversal of the transformed phenotype. Therefore HDAC inhibitors can have great therapeutic potential in the treatment of cell proliferative diseases or conditions (Marks et al., Nature Reviews: Cancer 1: 194-202, 2001)

The study of inhibitors of histone deacetylases (HDAC) indicates that indeed these enzymes play an important role in cell proliferation and differentiation. The inhibitor Trichostatin A (TSA) causes cell cycle arrest at both G1 and G2 phases, reverts the transformed phenotype of different cell lines, and induces differentiation of Friend leukemia cells and others. TSA (and suberoylanilide hydroxamic acid SAHA) have been reported to inhibit cell growth, induce terminal differentiation, and prevent the formation of tumours in mice (Finnin et al., Nature, 401: 188-193, 1999).

Trichostatin A has also been reported to be useful in the treatment of fibrosis, e.g. liver fibrosis and liver chirrhosis. (Geerts et al., European Patent Application EP 0 827 742, published 11 Mar. 1998).

Patent application DE 4228792 published on Mar. 3, 1994 describes compounds of general formula

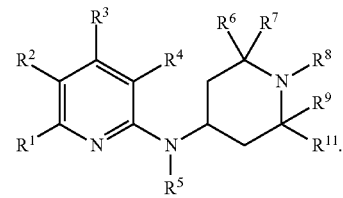

It provides processes for the preparation of these compounds, compositions comprising them, as well as their use as a fungicide.

Patent application WO 97/23216 published on Jul. 3, 1997 describes selective antagonists of N-methyl-D-aspartate receptor subtypes of general formula

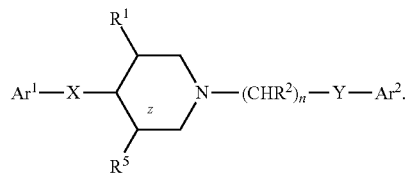

It presents pharmaceutical compositions containing these compounds and discloses the usefulness of these compounds for the treatment of neurological and other conditions.

U.S. Pat. No. 5,952,349 published on Sep. 14, 1999 discloses compounds of general formula

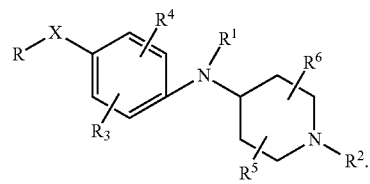

It further describes pharmaceutical compositions containing said compounds, the use of said compounds for the treatment of cognitive disorders and the use of said compounds in combination with acetylcholinesterase inhibitors.

Patent application WO 00/71516 published on Nov. 30, 2000 describes compounds of general formula A-Y-D-E-G-J-Z-L having activity against mammalian factor Xa, pharmaceutical compositions containing them and the use of said compounds for preventing or treating coagulation disorders.

Patent application WO 02/42271 describes compounds of general formula

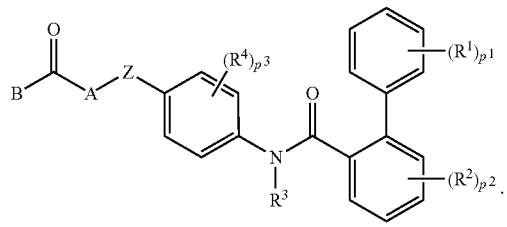

It further provides pharmaceutical compositions comprising these compounds as well as the use of these compounds as a medicine for the treatment of hyperlipidemia, obesity and type II diabetes.

Patent application WO 02/00651 published on Jan. 3, 2002 discloses inhibitors of trypsin-like serine protease enzymes of general formulas

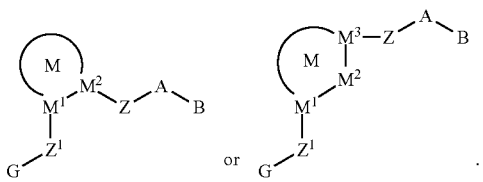

It presents pharmaceutical compositions containing said compounds and the use of said compounds as anti-coagulant agents for treatment and prevention of thromboembolic disorders.

Patent application WO 02/18335 published on Mar. 7, 2002 discloses compounds of general formula

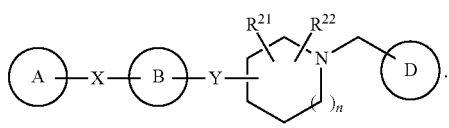

It provides for the use of said compounds in the treatment of CCR3-related diseases.

Patent application WO 03/000653 published on 3 Jan. 2003 describes compounds of general formula

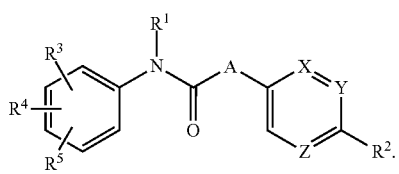

It further provides processes for the preparation of these compounds, compositions comprising them, as well as their use as a thrombin-inhibiting agent.

The compounds of the present invention differ from the prior art described in DE4228792, WO 97/23216, U.S. Pat. No. 5,952,349, WO 00/71516, WO 02/00651, WO 02/18335 and WO 03/000653 in structure and in activity.

Patent application WO01/38322 published on May 31, 2001 discloses amongst others inhibitors of histone deacetylase of general formula Cy-L$^1$-Ar—Y$^1$—C(O)—NH—Z, providing compositions and methods for treating cell proliferative diseases and conditions.

Patent application WO01/70675 published on 27 Sep. 2001 discloses inhibitors of histone deacetylase of formula Cy$^2$-Cy$^1$-X—Y$^1$—W and Cy-S(O)$_2$—NH—Y$^3$—W and further provides compositions and methods for treating cell proliferative diseases and conditions.

The problem to be solved is to provide histone deacetylase inhibitors with high enzymatic activity and also show advantageous properties such as cellular activity and increased bioavailability, preferably oral bioavailability, and have little or no side effects.

The novel compounds of the present invention solve the above described problem. The compounds differ from the prior art in structure.

The compounds of the present invention show excellent in-vitro histone deacetylase inhibiting enzymatic activity. The present compounds have advantageous properties with regard to cellular activity and specific properties with regard to inhibition of cell cycle progression at both G1 and G2 checkpoints (p21 induction capacity). The compounds of the present invention show good metabolic stability and high bioavailability and more particular they show oral bioavailability.

This invention concerns compounds of formula (I)

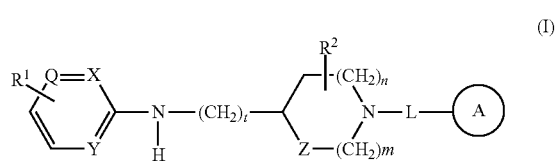

the N-oxide forms, the pharmaceutically acceptable addition salts and the stereo-chemically isomeric forms thereof, wherein n is 0, 1, 2 or 3 and when n is 0 then a direct bond is intended;
m is 0, 1, 2 or 3 and when m is 0 then a direct bond is intended;
t is 0 or 1 and when t is 0 then a direct bond is intended;
each Q is nitrogen or

each X is nitrogen or

each Y is nitrogen or

each Z is —CH$_2$— or —O—;
R$^1$ is —C(O)NR$^3$R$^4$, —N(H)C(O)R$^7$, —C(O)—C$_{1-6}$alkanediylSR$^7$, —NR$^8$C(O)N(OH)R$^7$, —NR$^8$C(O)C$_{1-6}$alkanediylSR$^7$, —NR$^8$C(O)C=N(OH)R$^7$ or another Zn-chelating-group wherein R$^3$ and R$^4$ are each independently selected from hydrogen, hydroxy, C$_{1-6}$alkyl, hydroxyC$_{1-6}$alkyl, aminoC$_{1-6}$alkyl or aminoaryl;
R$^7$ is independently selected from hydrogen, C$_{1-6}$alkyl, C$_{1-6}$alkylcarbonyl, arylC$_{1-6}$alkyl, C$_{1-6}$alkylpyrazinyl, pyridinone, pyrrolidinone or methylimidazolyl;
R$^8$ is independently selected from hydrogen or C$_{1-6}$alkyl;
R$^2$ is hydrogen, hydroxy, amino, hydroxyC$_{1-6}$alkyl, C$_{1-6}$alkyl, C$_{1-6}$alkyloxy, arylC$_{1-6}$alkyl, aminocarbonyl, hydroxycarbonyl, aminoC$_{1-6}$alkyl, aminocarbonylC$_{1-6}$alkyl, hydroxycarbonylC$_{1-6}$alkyl, hydroxyaminocarbonyl, C$_{1-6}$alkyloxycarbonyl, C$_{1-6}$alkylaminoC$_{1-6}$alkyl or di(C$_{1-6}$alkyl)aminoC$_{1-6}$alkyl;

-L- is a bivalent radical selected from $C_{1-6}$alkanediyl, carbonyl, sulfonyl, or $C_{1-6}$alkanediyl substituted with phenyl;
is a radical selected from
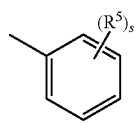 (a-1)
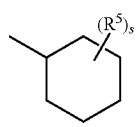 (a-2)
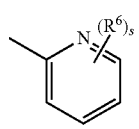 (a-3)
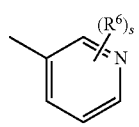 (a-4)
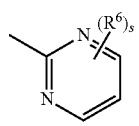 (a-5)
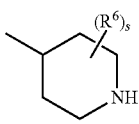 (a-6)
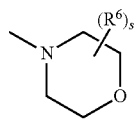 (a-7)
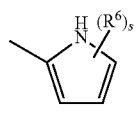 (a-8)
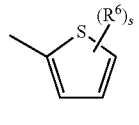 (a-9)
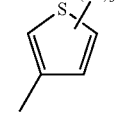 (a-10)
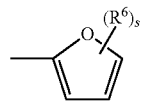 (a-11)
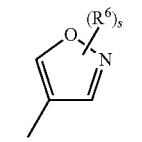 (a-12)
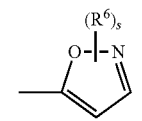 (a-13)
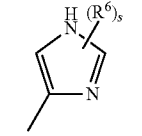 (a-14)
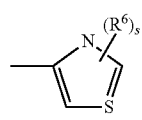 (a-15)
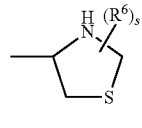 (a-16)
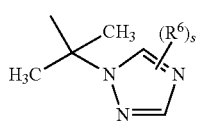 (a-17)
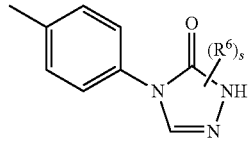 (a-18)
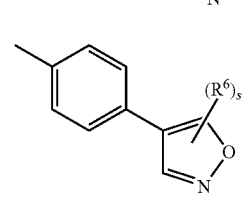 (a-19)
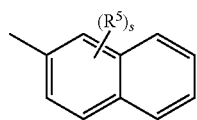 (a-20)
(a-21)

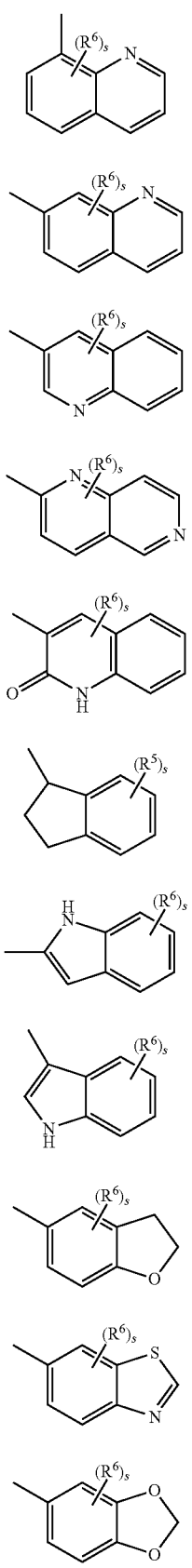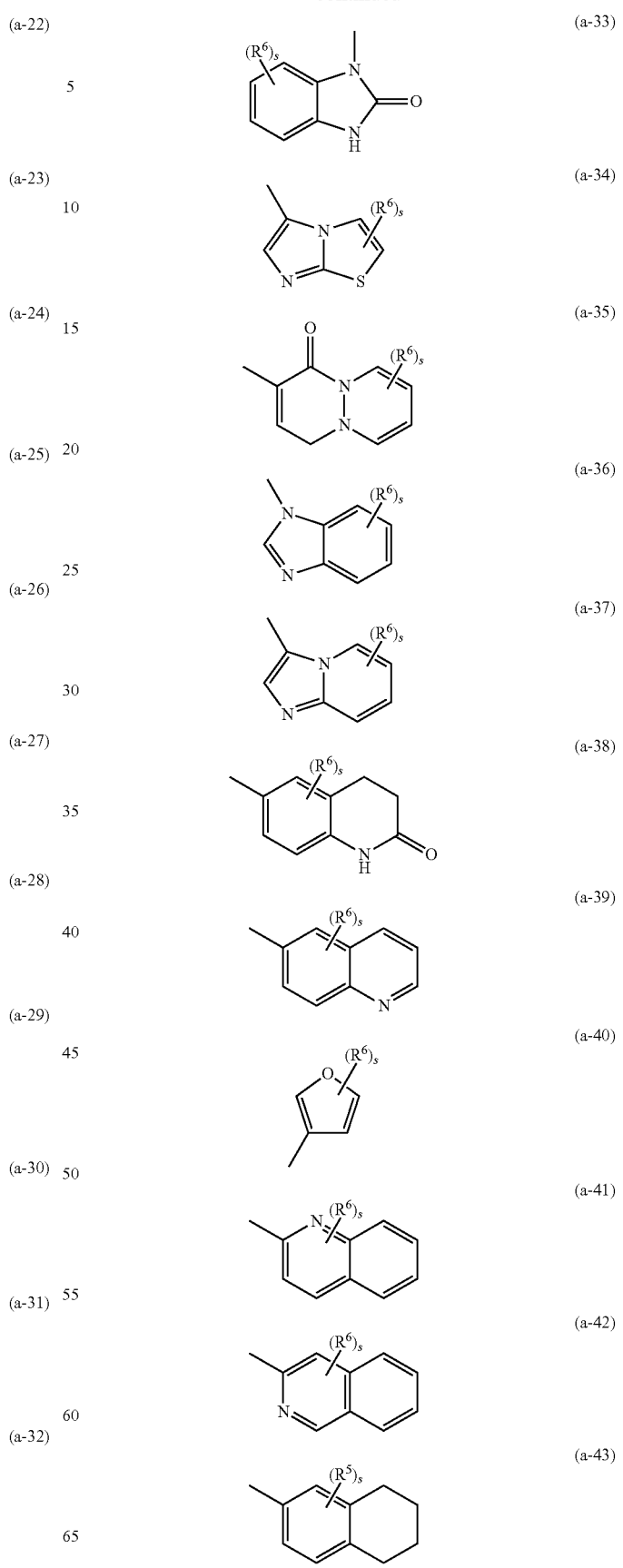

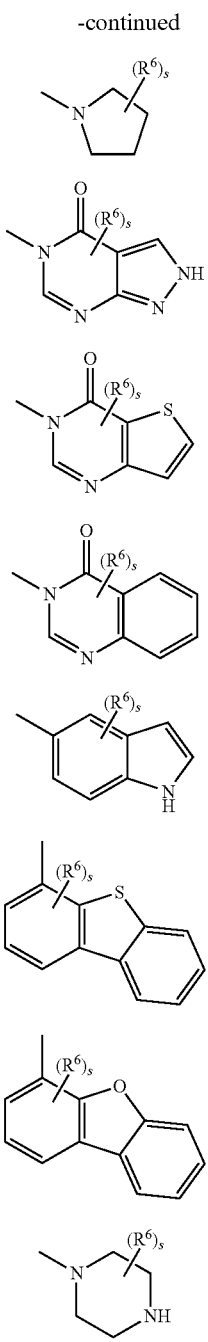

wherein each s is independently 0, 1, 2, 3, 4 or 5;
each $R^5$ and $R^6$ are independently selected from hydrogen; halo; hydroxy; amino; nitro; trihalo$C_{1-6}$alkyl; trihalo-$C_{1-6}$alkyloxy; $C_{1-6}$alkyl; $C_{1-6}$alkyl substituted with aryl and $C_{3-10}$cycloalkyl; $C_{1-6}$alkyloxy; $C_{1-6}$alkyloxy$C_{1-6}$alkyloxy; $C_{1-6}$alkylcarbonyl; $C_{1-6}$alkyloxycarbonyl; $C_{1-6}$alkylsulfonyl; cyano$C_{1-6}$alkyl; hydroxy$C_{1-6}$alkyl; hydroxy-$C_{1-6}$alkyloxy; hydroxy$C_{1-6}$alkylamino; amino$C_{1-6}$alkyloxy; di($C_{1-6}$alkyl)aminocarbonyl; di(hydroxy$C_{1-6}$alkyl)amino; (aryl)($C_{1-6}$alkyl)amino; di($C_{1-6}$alkyl)amino$C_{1-6}$alkyloxy; di($C_{1-6}$alkyl)amino$C_{1-6}$alkylamino; di($C_{1-6}$alkyl)amino$C_{1-6}$alkylamino$C_{1-6}$alkyl; arylsulfonyl; arylsulfonylamino; aryloxy; aryloxy$C_{1-6}$alkyl; aryl$C_{2-6}$alkenediyl; di($C_{1-6}$alkyl)amino; di($C_{1-6}$alkyl)amino$C_{1-6}$alkyl; di($C_{1-6}$alkyl)amino($C_{1-6}$alkyl)amino; di($C_{1-6}$alkyl) amino($C_{1-6}$alkyl)amino$C_{1-6}$alkyl; di($C_{1-6}$alkyl)aminoC$_{1-6}$alkyl($C_{1-6}$alkyl)amino; di($C_{1-6}$alkyl)amino$C_{1-6}$alkyl($C_{1-6}$alkyl)amino$C_{1-6}$alkyl; aminosulfonylamino($C_{1-6}$alkyl)amino; aminosulfonylamino($C_{1-6}$alkyl)amino$C_{1-6}$alkyl; di($C_{1-6}$alkyl)aminosulfonylamino($C_{1-6}$alkyl)amino; di($C_{1-6}$alkyl)aminosulfonylamino($C_{1-6}$alkyl)amino$C_{1-6}$alkyl; cyano; thiophenyl; thiophenyl substituted with di($C_{1-6}$alkyl)amino$C_{1-6}$alkyl($C_{1-6}$alkyl)amino$C_{1-6}$alkyl, di($C_{1-6}$alkyl)amino$C_{1-6}$alkyl, $C_{1-6}$alkylpiperazinyl$C_{1-6}$alkyl, hydroxy$C_{1-6}$alkylpiperazinyl$C_{1-6}$alkyl, hydroxy-$C_{1-6}$alkyloxy$C_{1-6}$alkylpiperazinyl$C_{1-6}$alkyl, di($C_{1-6}$alkyl)aminosulfonylpiperazinyl$C_{1-6}$alkyl, $C_{1-6}$alkyloxypiperidinyl, $C_{1-6}$alkyloxypiperidinyl$C_{1-6}$alkyl, morpholinyl$C_{1-6}$alkyl, hydroxy$C_{1-6}$alkyl($C_{1-6}$alkyl)amino$C_{1-6}$alkyl, or di(hydroxy$C_{1-6}$alkyl)amino$C_{1-6}$alkyl; furanyl; furanyl substituted with hydroxy$C_{1-6}$alkyl; benzofuranyl; imidazolyl; oxazolyl; oxazolyl substituted with aryl and $C_{1-6}$alkyl; $C_{1-6}$alkyltriazolyl; tetrazolyl; pyrrolidinyl; pyrrolyl; piperidinyl$C_{1-6}$alkyloxy; morpholinyl; $C_{1-6}$alkylmorpholinyl; morpholinyl$C_{1-6}$alkyloxy; morpholinyl$C_{1-6}$alkyl; morpholinyl$C_{1-6}$alkylamino; morpholinyl$C_{1-6}$alkylamino$C_{1-6}$alkyl; piperazinyl; $C_{1-6}$alkylpiperazinyl; $C_{1-6}$alkylpiperazinyl$C_{1-6}$alkyloxy; piperazinyl$C_{1-6}$alkyl; naphtalenylsulfonylpiperazinyl; naphtalenylsulfonylpiperidinyl; naphtalenylsulfonyl; $C_{1-6}$alkylpiperazinyl$C_{1-6}$alkyl; $C_{1-6}$alkylpiperazinyl$C_{1-6}$alkylamino; $C_{1-6}$alkylpiperazinyl$C_{1-6}$alkylamino$C_{1-6}$alkyl; $C_{1-6}$alkylpiperazinylsulfonyl; aminosulfonylpiperazinyl$C_{1-6}$alkyloxy; aminosulfonylpiperazinyl; aminosulfonylpiperazinyl$C_{1-6}$alkyl; di($C_{1-6}$alkyl)aminosulfonylpiperazinyl; di($C_{1-6}$alkyl)aminosulfonylpiperazinyl$C_{1-6}$alkyl; hydroxy$C_{1-6}$alkylpiperazinyl; hydroxy$C_{1-6}$alkylpiperazinyl$C_{1-6}$alkyl; $C_{1-6}$alkyloxypiperidinyl; $C_{1-6}$alkyloxypiperidinyl$C_{1-6}$alkyl; piperidinylamino$C_{1-6}$alkylamino; piperidinylamino$C_{1-6}$alkylamino$C_{1-6}$alkyl; ($C_{1-6}$alkylpiperidinyl)(hydroxy$C_{1-6}$alkyl)amino$C_{1-6}$alkylamino; ($C_{1-6}$alkylpiperidinyl)(hydroxy$C_{1-6}$alkyl)amino$C_{1-6}$alkylamino$C_{1-6}$alkyl; hydroxy$C_{1-6}$alkyloxy$C_{1-6}$alkylpiperazinyl; hydroxy$C_{1-6}$alkyloxy$C_{1-6}$alkylpiperazinyl$C_{1-6}$alkyl; (hydroxy$C_{1-6}$alkyl)($C_{1-6}$alkyl)amino; (hydroxy$C_{1-6}$alkyl)($C_{1-6}$alkyl)amino$C_{1-6}$alkyl; hydroxy$C_{1-6}$alkylamino$C_{1-6}$alkyl; di(hydroxy$C_{1-6}$alkyl)amino$C_{1-6}$alkyl; pyrrolidinyl$C_{1-6}$alkyl; pyrrolidinyl$C_{1-6}$alkyloxy; pyrazolyl; thiopyrazolyl; pyrazolyl substituted with two substituents selected from $C_{1-6}$alkyl or trihalo$C_{1-6}$alkyl; pyridinyl; pyridinyl substituted with $C_{1-6}$alkyloxy, aryloxy or aryl; pyrimidinyl; tetrahydropyrimidinylpiperazinyl; tetrahydropyrimidinylpiperazinyl$C_{1-6}$alkyl; quinolinyl; indolyl; phenyl; phenyl substituted with one, two or three substituents independently selected from halo, amino, nitro, $C_{1-6}$alkyl, $C_{1-6}$alkyloxy, hydroxy$C_{1-4}$alkyl, trifluoromethyl, trifluoromethyloxy, hydroxy$C_{1-4}$alkyloxy, $C_{1-4}$alkylsulfonyl, $C_{1-4}$alkyloxy$C_{1-4}$alkyloxy, $C_{1-4}$alkyloxycarbonyl, amino$C_{1-4}$alkyloxy, di($C_{1-4}$alkyl)amino$C_{1-4}$alkyloxy, di($C_{1-4}$alkyl)amino, di($C_{1-4}$alkyl)aminocarbonyl, di($C_{1-4}$alkyl)amino$C_{1-4}$alkyl, di($C_{1-4}$alkyl)amino$C_{1-4}$alkylamino$C_{1-4}$alkyl, di($C_{1-4}$alkyl)amino($C_{1-4}$alkyl)amino, di($C_{1-4}$alkyl)amino($C_{1-4}$alkyl)amino$C_{1-4}$alkyl, di($C_{1-4}$alkyl)amino$C_{1-4}$alkyl($C_{1-4}$alkyl)amino, di($C_{1-4}$alkyl)amino$C_{1-4}$alkyl($C_{1-4}$alkyl)amino$C_{1-4}$alkyl, aminosulfonylamino($C_{1-4}$alkyl)amino, aminosulfonylamino($C_{1-4}$alkyl)amino$C_{1-4}$alkyl, di($C_{1-4}$alkyl)aminosulfonylamino($C_{1-4}$alkyl)amino, di($C_{1-4}$alkyl)aminosulfonylamino($C_{1-4}$alkyl)amino$C_{1-6}$alkyl, cyano, piperidinyl$C_{1-4}$alkyloxy, pyrrolidinyl$C_{1-4}$alkyloxy, aminosulfonylpiperazinyl, aminosulfonylpiperazinyl$C_{1-4}$alkyl, di($C_{1-4}$alkyl)aminosulfonylpiperazinyl, di($C_{1-4}$alkyl)aminosulfonylpiperazinyl$C_{1-4}$alkyl, hydroxyC$_{1-4}$alkylpiperazinyl, hydroxyC$_{1-4}$alkylpiperazinylC$_{1-4}$alkyl, C$_{1-4}$alkyloxypiperidinyl, C$_{1-4}$alkyloxypiperidinylC$_{1-4}$alkyl, hydroxyC$_{1-4}$alkyloxyC$_{1-4}$alkylpiperazinyl, hydroxyC$_{1-4}$alkyloxyC$_{1-4}$alkylpiperazinylC$_{1-4}$alkyl, (hydroxyC$_{1-4}$alkyl)(C$_{1-4}$alkyl)amino, (hydroxyC$_{1-4}$alkyl)(C$_{1-4}$alkyl)aminoC$_{1-4}$alkyl, di(hydroxyC$_{1-4}$alkyl)amino, di(hydroxyC$_{1-4}$alkyl)aminoC$_{1-4}$alkyl, furanyl, furanyl substituted with —CH=CH—CH=CH—, pyrrolidinylC$_{1-4}$alkyl, pyrrolidinylC$_{1-4}$alkyloxy, morpholinyl, morpholinylC$_{1-4}$alkyloxy, morpholinylC$_{1-4}$alkyl, morpholinylC$_{1-4}$alkylamino, morpholinylC$_{1-4}$alkylaminoC$_{1-4}$alkyl, piperazinyl, C$_{1-4}$alkylpiperazinyl, C$_{1-4}$alkylpiperazinylC$_{1-4}$alkyloxy, piperazinylC$_{1-4}$alkyl, C$_{1-4}$alkylpiperazinylC$_{1-4}$alkyl, C$_{1-4}$alkylpiperazinylC$_{1-4}$alkylamino, C$_{1-4}$alkylpiperazinylC$_{1-4}$alkylaminoC$_{1-6}$alkyl, tetrahydropyrimidinylpiperazinyl, tetrahydropyrimidinylpiperazinylC$_{1-4}$alkyl, piperidinylaminoC$_{1-4}$alkylamino, piperidinylaminoC$_{1-4}$alkylaminoC$_{1-4}$alkyl, (C$_{1-4}$alkylpiperidinyl)(hydroxyC$_{1-4}$alkyl)aminoC$_{1-4}$alkylamino, (C$_{1-4}$alkylpiperidinyl)(hydroxyC$_{1-4}$alkyl)aminoC$_{1-4}$alkylaminoC$_{1-4}$alkyl, pyridinylC$_{1-4}$alkyloxy, hydroxyC$_{1-4}$alkylamino, hydroxyC$_{1-4}$alkylaminoC$_{1-4}$alkyl, di(C$_{1-4}$alkyl)aminoC$_{1-4}$alkylamino, aminothiadiazolyl, aminosulfonylpiperazinylC$_{1-4}$alkyloxy, or thiophenylC$_{1-4}$alkylamino;

each R$^5$ and R$^6$ can be placed on the nitrogen in replacement of the hydrogen;

aryl in the above is phenyl, or phenyl substituted with one or more substituents each independently selected from halo, C$_{1-6}$alkyl, C$_{1-6}$alkyloxy, trifluoromethyl, cyano or hydroxycarbonyl.

The term "histone deacetylase inhibitor" or "inhibitor of histone deacetylase" is used to identify a compound, which is capable of interacting with a histone deacetylase and inhibiting its activity, more particularly its enzymatic activity. Inhibiting histone deacetylase enzymatic activity means reducing the ability of a histone deacetylase to remove an acetyl group from a histone. Preferably, such inhibition is specific, i.e. the histone deacetylase inhibitor reduces the ability of a histone deacetylase to remove an acetyl group from a histone at a concentration that is lower than the concentration of the inhibitor that is required to produce some other, unrelated biological effect.

As used in the foregoing definitions and hereinafter, halo is generic to fluoro, chloro, bromo and iodo; C$_{1-4}$alkyl defines straight and branched chain saturated hydrocarbon radicals having from 1 to 4 carbon atoms such as, e.g. methyl, ethyl, propyl, butyl, 1-methylethyl, 2-methylpropyl and the like; C$_{1-6}$alkyl includes C$_{1-4}$alkyl and the higher homologues thereof having 5 to 6 carbon atoms such as, for example, pentyl, 2-methyl-butyl, hexyl, 2-methylpentyl and the like; C$_{1-6}$alkanediyl defines bivalent straight and branched chained saturated hydrocarbon radicals having from 1 to 6 carbon atoms such as, for example, methylene, 1,2-ethanediyl, 1,3-propanediyl 1,4-butanediyl, 1,5-pentanediyl, 1,6-hexanediyl and the branched isomers thereof such as, 2-methylpentanediyl, 3-methylpentanediyl, 2,2-dimethylbutanediyl, 2,3-dimethylbutanediyl and the like; trihaloC$_{1-6}$alkyl defines C$_{1-6}$alkyl containing three identical or different halo substituents for example trifluoromethyl; C$_{2-6}$alkenediyl defines bivalent straight and branched chain hydrocarbon radicals containing one double bond and having from 2 to 6 carbon atoms such as, for example, ethenediyl, 2-propenediyl, 3-butenediyl, 2-pentenediyl, 3-pentenediyl, 3-methyl-2-butenediyl, and the like; and aminoaryl defines aryl substituted with amino.

The term "another Zn-chelating group" refers to a group, which is capable of interacting with a Zn-ion, which can be present at an enzymatic binding site.

Pharmaceutically acceptable addition salts encompass pharmaceutically acceptable acid addition salts and pharmaceutically acceptable base addition salts. The pharmaceutically acceptable acid addition salts as mentioned hereinabove are meant to comprise the therapeutically active non-toxic acid addition salt forms, which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, trifluoroacetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formula (I) which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "acid or base addition salts" also comprises the hydrates and the solvent addition forms, which the compounds of formula (I) are able to form. Examples of such forms are e.g. hydrates, alcoholates and the like.

The term "stereochemically isomeric forms of compounds of formula (I)", as used herein, defines all possible compounds made up of the same atoms bonded by the same sequence of bonds but having different three-dimensional structures, which are not interchangeable, which the compounds of formula (I) may possess. Unless otherwise mentioned or indicated, the chemical designation of a compound encompasses the mixture of all possible stereochemically isomeric forms, which said compound might possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

The N-oxide forms of the compounds of formula (I) are meant to comprise those compounds of formula (I) wherein one or several nitrogen atoms are oxidized to the so-called N-oxide, particularly those N-oxides wherein one or more of the piperidine-, piperazine or pyridazinyl-nitrogens are N-oxidized.

Some of the compounds of formula (I) may also exist in their tautomeric forms. Such forms although not explicitly indicated in the above formula are intended to be included within the scope of the present invention.

Whenever used hereinafter, the term "compounds of formula (I)" is meant to include also the pharmaceutically acceptable addition salts and all stereoisomeric forms.

As used herein, the terms "histone deacetylase" and "HDAC" are intended to refer to any one of a family of enzymes that remove acetyl groups from the ε-amino groups of lysine residues at the N-terminus of a histone. Unless otherwise indicated by context, the term "histone" is meant to refer to any histone protein, including H1, H2A, H2B, H3, H4, and H5, from any species. Human HDAC proteins or gene products, include, but are not limited to, HDAC-1, HDAC-2, HDAC-3, HDAC-4, HDAC-5, HDAC-6, HDAC-7, HDAC-8, HDAC-9 and HDAC-10. The histone deacetylase can also be derived from a protozoal or fungal source.

A first group of interesting compounds consists of those compounds of formula (I) wherein one or more of the following restrictions apply:
a) n is 0, 1 or 2;
b) m is 0, 1 or 2;
c) each Q is

d) each X is nitrogen;
e) $R^1$ is —C(O)NH(OH);
f) $R^2$ is hydrogen;
g) -L- is a bivalent radical selected from carbonyl, sulfonyl, or $C_{1-6}$alkanediyl substituted with phenyl;
h)

is a radical selected from (a-1), (a-20) or (a-43);
i) each s is independently 0 or 1;
j) each $R^5$ is independently selected from hydrogen or phenyl.

A second group of interesting compounds consists of those compounds of formula (I) wherein one or more of the following restrictions apply:
a) n is 0, 1 or 2;
b) m is 1 or 2;
c) each Q is

d) each X is nitrogen;
d) $R^1$ is —C(O)NH(OH);
f) $R^2$ is hydrogen;
e) -L- is a bivalent radical selected from carbonyl or sulfonyl;
f)

is a radical selected from (a-1) or (a-20);
g) each s is independently 0 or 1;
h) each $R^5$ is independently selected from hydrogen or aryl.

A third group of interesting compounds consists of those compounds of formula (I) wherein $R^1$ is —C(O)NH(OH).

A fourth group of interesting compounds consists of those compounds of formula (I) wherein one or more of the following restrictions apply:
a) t is 0;
b) $R^1$ is —C(O)NR$^3$R$^4$, —C(O)—C$_{1-6}$alkanediylSR$^7$, —NR$^8$C(O)N(OH)R$^7$, —NR$^8$C(O)C$_{1-6}$alkanediylSR$^7$, —NR$^8$C(O)C=N(OH)R$^7$ or another Zn-chelating-group wherein $R^3$ and $R^4$ are each independently selected from hydrogen, hydroxy, hydroxyC$_{1-6}$alkyl or aminoC$_{1-6}$alkyl;
c) $R^2$ is hydrogen, hydroxy, amino, hydroxyC$_{1-6}$alkyl, C$_{1-6}$alkyl, C$_{1-6}$alkyloxy, arylC$_{1-6}$alkyl, aminocarbonyl, aminoC$_{1-6}$alkyl, C$_{1-6}$alkylaminoC$_{1-6}$alkyl or di(C$_{1-6}$alkyl)aminoC$_{1-6}$alkyl;
d) -L- is a bivalent radical selected from C$_{1-6}$alkanediyl, carbonyl or sulfonyl;
e)

is a radical selected from (a-1), (a-3), (a-4), (a-5), (a-6), (a-7), (a-8), (a-9), (a-10), (a-11), (a-12), (a-13), (a-14), (a-15), (a-16), (a-17), (a-18), (a-19), (a-20), (a-21), (a-22), (a-23), (a-24), (a-25), (a-26), (a-28), (a-29), (a-30), (a-31), (a-32), (a-33), (a-34), (a-35), (a-36), (a-37), (a-38), (a-39), (a-40), (a-41), (a-42), (a-44), (a-45), (a-46), (a-47), (a-48) or (a-51);
f) each s is independently 0, 1, 2, 3 or 4;
g) $R^5$ is hydrogen; halo; hydroxy; amino; nitro; trihaloC$_{1-6}$alkyl; trihaloC$_{1-6}$alkyloxy; C$_{1-6}$alkyl; C$_{1-6}$alkyloxy; C$_{1-6}$alkylcarbonyl; C$_{1-6}$alkyloxycarbonyl; C$_{1-6}$alkylsulfonyl; hydroxyC$_{1-6}$alkyl; aryloxy; di(C$_{1-6}$alkyl)amino; cyano; thiophenyl; furanyl; furanyl substituted with hydroxyC$_{1-6}$alkyl; benzofuranyl; imidazolyl; oxazolyl; oxazolyl substituted with aryl and C$_{1-6}$alkyl; C$_{1-6}$alkyltriazolyl; tetrazolyl; pyrrolidinyl; pyrrolyl; morpholinyl; C$_{1-6}$alkylmorpholinyl; piperazinyl; C$_{1-6}$alkylpiperazinyl; hydroxyC$_{1-6}$alkylpiperazinyl; C$_{1-6}$alkyloxypiperidinyl; pyrazoly; pyrazolyl substituted with one or two substituents selected from C$_{1-6}$alkyl or trihaloC$_{1-6}$alkyl; pyridinyl; pyridinyl substituted with C$_{1-6}$alkyloxy, aryloxy or aryl; pyrimidinyl; quinolinyl; indole; phenyl; or phenyl substituted with one or two substituents independently selected from halo, C$_{1-6}$alkyl, C$_{1-6}$alkyloxy or trifluoromethyl;
h) $R^6$ is hydrogen; halo; hydroxy; amino; nitro; trihaloC$_{1-6}$alkyl; trihaloC$_{1-6}$alkyloxy; C$_{1-6}$alkyl; C$_{1-6}$alkyloxy; C$_{1-6}$alkylcarbonyl; C$_{1-6}$alkyloxycarbonyl; C$_{1-6}$alkylsulfonyl; hydroxyC$_{1-6}$alkyl; aryloxy; di(C$_{1-6}$alkyl)amino; cyano; pyridinyl; phenyl; or phenyl substituted with one or two substituents independently selected from halo, C$_{1-6}$alkyl, C$_{1-6}$alkyloxy or trifluoromethyl.

A group of preferred compounds consists of those compounds of formula (I) wherein
t is 0;
$R^1$ is —C(O)NR$^3$R$^4$, —C(O)—C$_{1-6}$alkanediylSR$^7$, —NR$^8$C(O)N(OH)R$^7$, —NR$^8$C(O)C$_{1-6}$alkanediylSR$^7$, —NR$^8$C(O)C=N(OH)R$^7$ or another Zn-chelating-group wherein $R^3$ and $R^4$ are each independently selected from hydrogen, hydroxy, hydroxyC$_{1-6}$alkyl or aminoC$_{1-6}$alkyl;
$R^2$ is hydrogen, hydroxy, amino, hydroxyC$_{1-6}$alkyl, C$_{1-6}$alkyl, C$_{1-6}$alkyloxy, arylC$_{1-6}$alkyl, aminocarbonyl, aminoC$_{1-6}$alkyl, C$_{1-6}$alkylaminoC$_{1-6}$alkyl or di(C$_{1-6}$alkyl)aminoC$_{1-6}$alkyl;
-L- is a bivalent radical selected from C$_{1-6}$alkanediyl, carbonyl or sulfonyl;

is a radical selected from (a-1), (a-3), (a-4), (a-5), (a-6), (a-7), (a-8), (a-9), (a-10), (a-11), (a-12), (a-13), (a-14), (a-15), (a-16), (a-17), (a-18), (a-19), (a-20), (a-21), (a-22), (a-23), (a-24), (a-25), (a-26), (a-28), (a-29), (a-30), (a-31), (a-32), (a-33), (a-34), (a-35), (a-36), (a-37), (a-38), (a-39), (a-40), (a-41), (a-42), (a-44), (a-45), (a-46), (a-47), (a-48) or (a-51); s is 0, 1, 2, 3 or 4;

$R^5$ is hydrogen; halo; hydroxy; amino; nitro; trihalo$C_{1-6}$alkyl; trihalo$C_{1-6}$alkyloxy; $C_{1-6}$alkyl; $C_{1-6}$alkyloxy; $C_{1-6}$alkylcarbonyl; $C_{1-6}$alkyloxycarbonyl; $C_{1-6}$alkylsulfonyl; hydroxy$C_{1-6}$alkyl; aryloxy; di($C_{1-6}$alkyl)amino; cyano; thiophenyl; furanyl; furanyl substituted with hydroxy-$C_{1-6}$alkyl; benzofuranyl; imidazolyl; oxazolyl; oxazolyl substituted with aryl and $C_{1-6}$alkyl; $C_{1-6}$alkyltriazolyl; tetrazolyl; pyrrolidinyl; pyrrolyl; morpholinyl; $C_{1-6}$alkylmorpholinyl; piperazinyl; $C_{1-6}$alkylpiperazinyl; hydroxy$C_{1-6}$alkylpiperazinyl; $C_{1-6}$alkyloxypiperidinyl; pyrazoly; pyrazolyl substituted with one or two substituents selected from $C_{1-6}$alkyl or trihalo$C_{1-6}$alkyl; pyridinyl; pyridinyl substituted with $C_{1-6}$alkyloxy, aryloxy or aryl; pyrimidinyl; quinolinyl; indole; phenyl; or phenyl substituted with one or two substituents independently selected from halo, $C_{1-6}$alkyl, $C_{1-6}$alkyloxy or trifluoromethyl; and $R^6$ is hydrogen; halo; hydroxy; amino; nitro; trihalo$C_{1-6}$alkyl; trihalo$C_{1-6}$alkyloxy; $C_{1-6}$alkyl; $C_{1-6}$alkyloxy; $C_{1-6}$alkylcarbonyl; $C_{1-6}$alkyloxycarbonyl; $C_{1-6}$alkylsulfonyl; hydroxy$C_{1-6}$alkyl; aryloxy; di($C_{1-6}$alkyl)amino; cyano; pyridinyl; phenyl; or phenyl substituted with one or two substituents independently selected from halo, $C_{1-6}$alkyl, $C_{1-6}$alkyloxy or trifluoromethyl.

A group of more preferred compounds consists of those compounds of formula (I) wherein n is 0, 1 or 2; m is 0, 1 or 2; each Q is

each X is nitrogen; $R^1$ is —C(O)NH(OH); $R^2$ is hydrogen; -L- is a bivalent radical selected from carbonyl, sulfonyl, or $C_{1-6}$alkanediyl substituted with phenyl;

is a radical selected from (a-1), (a-20) or (a-43); s is 0 or 1; and each $R^5$ is independently selected from hydrogen or phenyl.

A group of even more preferred compounds consists of those compounds of formula (I) wherein n is 0, 1 or 2; m is 1 or 2; each Q is

each X is nitrogen; $R^1$ is —C(O)NH(OH); $R^2$ is hydrogen; -L- is a bivalent radical selected from carbonyl or sulfonyl;

is a radical selected from (a-1) or (a-20); each s is independently 0 or 1; and each $R^5$ is independently selected from hydrogen or aryl.

Most preferred compounds are compounds No. 1, No. 3, No. 5, No. 4, No. 14, No. 12, No. 7. No. 8 or No. 9.

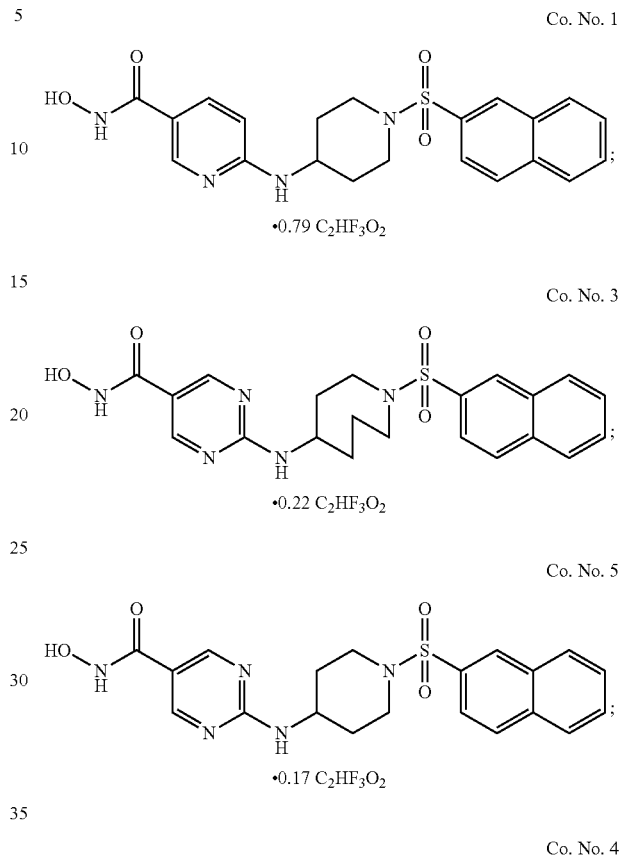

Co. No. 1

•0.79 $C_2HF_3O_2$

Co. No. 3

•0.22 $C_2HF_3O_2$

Co. No. 5

•0.17 $C_2HF_3O_2$

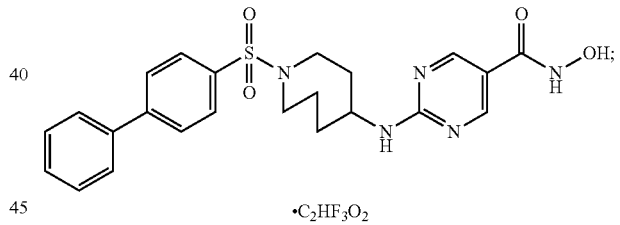

Co. No. 4

•$C_2HF_3O_2$

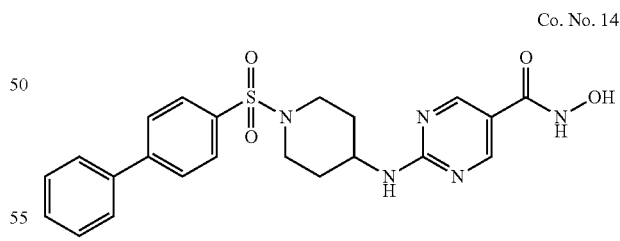

Co. No. 14

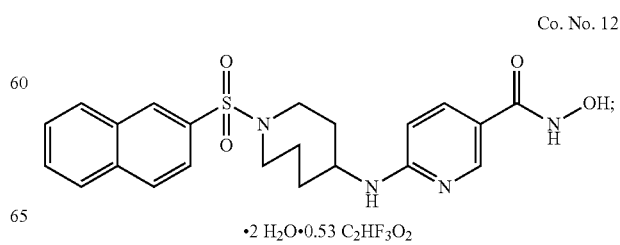

Co. No. 12

•2 $H_2O$•0.53 $C_2HF_3O_2$

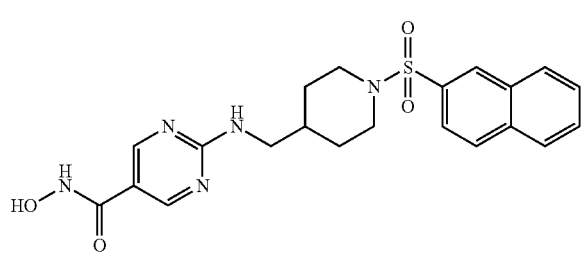
Co. No. 7

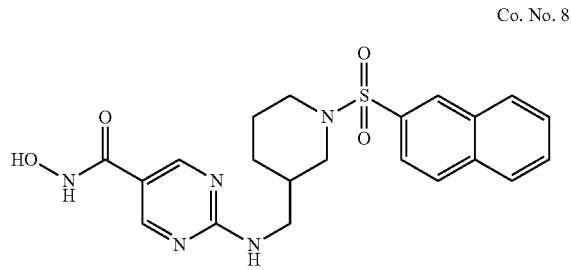
Co. No. 8

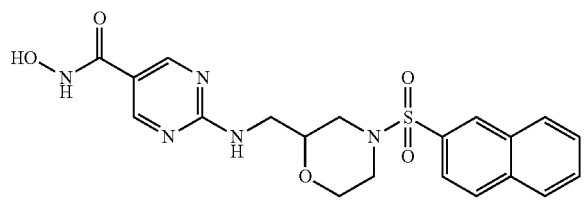
Co. No. 9

The compounds of formula (I) and their pharmaceutically acceptable salts and N-oxides and stereochemically isomeric forms thereof may be prepared in conventional manner.

A general synthesis route is encompassed as example:

a) Hydroxamic acids of formula (I) wherein $R^1$ is —C(O)NH(OH), said compounds being referred to as compounds of formula (I-a), may be prepared by reacting an intermediate of formula (II) with an appropriate acid, such as for example, trifluoro acetic acid. Said reaction is performed in an appropriate solvent, such as, for example, methanol.

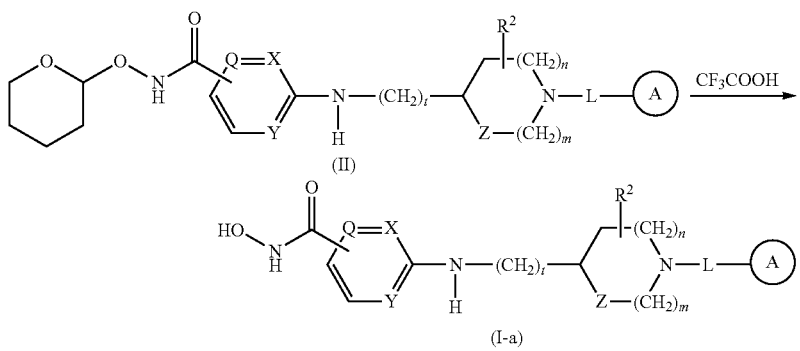

b) intermediates of formula (II) may be prepared by reacting an intermediate of formula (III) with an intermediate of formula (IV) in the presence of appropriate reagents such as N'-(ethylcarbonimidoyl)-N,N-dimethyl-1,3-propanediamine, monohydrochloride (EDC) and 1-hydroxy-1H-benzotriazole (HOBT). The reaction may be performed in a suitable solvent such as a mixture of dichloromethane and tetrahydrofuran.

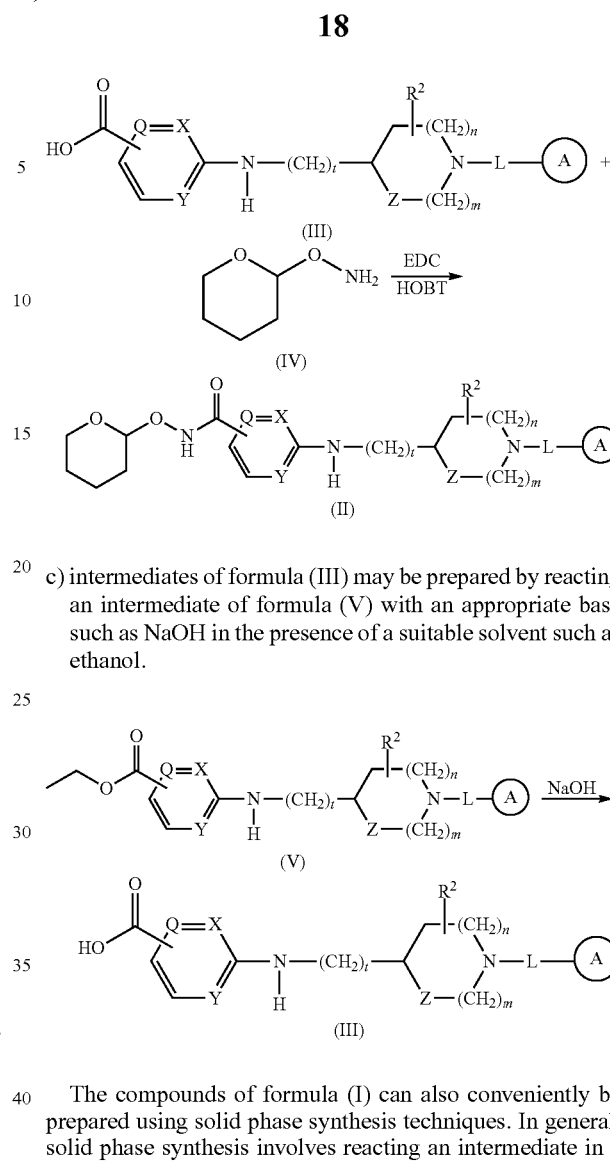

c) intermediates of formula (III) may be prepared by reacting an intermediate of formula (V) with an appropriate base such as NaOH in the presence of a suitable solvent such as ethanol.

The compounds of formula (I) can also conveniently be prepared using solid phase synthesis techniques. In general, solid phase synthesis involves reacting an intermediate in a synthesis with a polymer support. This polymer-supported intermediate can then be carried on through a number of synthesis steps. After each step, filtering the resin and washing it numerous times with various solvents remove impurities. At each step the resin can be split up to react with various intermediates in the next step thus allowing for the synthesis of a large number of compounds. After the last step in the procedure the resin is treated with a reagent or process to cleave the resin from the sample. More detailed explanation of the techniques used in solid phase chemistry is described in for example "The Combinatorial Index" (B. Bunin, Academic Press) and Novabiochem's 1999 Catalogue & Peptide Synthesis Handbook (Novabiochem AG, Switzerland) both incorporated herein by reference.

The compounds of formula (I) and some of the intermediates may have at least one stereogenic centre in their structure. This stereogenic centre may be present in an R or an S configuration.

The compounds of formula (I) as prepared in the hereinabove described processes are generally racemic mixtures of enantiomers, which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated there from by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

The compounds of formula (I), the pharmaceutically acceptable acid addition salts and stereoisomeric forms thereof have valuable pharmacological properties in that they have a histone deacetylase (HDAC) inhibitory effect.

This invention provides a method for inhibiting the abnormal growth of cells, including transformed cells, by administering an effective amount of a compound of the invention. Abnormal growth of cells refers to cell growth independent of normal regulatory mechanisms (e.g. loss of contact inhibition). This includes the inhibition of tumour growth both directly by causing growth arrest, terminal differentiation and/or apoptosis of cancer cells, and indirectly, by inhibiting neovascularization of tumours.

This invention also provides a method for inhibiting tumour growth by administering an effective amount of a compound of the present invention, to a subject, e.g. a mammal (and more particularly a human) in need of such treatment. In particular, this invention provides a method for inhibiting the growth of tumours by the administration of an effective amount of the compounds of the present invention. Examples of tumours which may be inhibited, but are not limited to, lung cancer (e.g. adenocarcinoma and including non-small cell lung cancer), pancreatic cancers (e.g. pancreatic carcinoma such as, for example exocrine pancreatic carcinoma), colon cancers (e.g. colorectal carcinomas, such as, for example, colon adenocarcinoma and colon adenoma), prostate cancer including the advanced disease, hematopoietic tumours of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MDS), tumours of mesenchymal origin (e.g. fibrosarcomas and rhabdomyosarcomas), melanomas, teratocarcinomas, neuroblastomas, gliomas, benign tumour of the skin (e.g. keratoacanthomas), breast carcinoma (e.g. advanced breast cancer), kidney carcinoma, ovary carcinoma, bladder carcinoma and epidermal carcinoma.

The compound according to the invention may be used for other therapeutic purposes, for example:

a) the sensitisation of tumours to radiotherapy by administering the compound according to the invention before, during or after irradiation of the tumour for treating cancer;

b) treating arthropathies and osteopathological conditions such as rheumatoid arthritis, osteoarthritis, juvenile arthritis, gout, polyarthritis, psoriatic arthritis, ankylosing spondylitis and systemic lupus erythematosus;

c) inhibiting smooth muscle cell proliferation including vascular proliferative disorders, atherosclerosis and restenosis;

d) treating inflammatory conditions and dermal conditions such as ulcerative colitis, Crohn's disease, allergic rhinitis, graft vs. host disease, conjunctivitis, asthma, ARDS, Behcets disease, transplant rejection, uticaria, allergic dermatitis, alopecia greata, scleroderma, exanthema, eczema, dermatomyositis, acne, diabetes, systemic lupus erythematosus, Kawasaki's disease, multiple sclerosis, emphysema, cystic fibrosis and chronic bronchitis;

e) treating endometriosis, uterine fibroids, dysfunctional uterine bleeding and endometrial hyperplasia;

f) treating ocular vascularisation including vasculopathy affecting retinal and choroidal vessels;

g) treating a cardiac dysfunction;

h) inhibiting immunosuppressive conditions such as the treatment of HIV infections;

i) treating renal dysfunction;

j) suppressing endocrine disorders;

k) inhibiting dysfunction of gluconeogenesis;

l) treating a neuropathology for example Parkinson's disease or a neuropathology that results in a cognitive disorder, for example, Alzheimer's disease or polyglutamine related neuronal diseases;

m) inhibiting a neuromuscular pathology, for example, amylotrophic lateral sclerosis;

n) treating spinal muscular atrophy;

o) treating other pathologic conditions amenable to treatment by potentiating expression of a gene;

p) enhancing gene therapy.

Hence, the present invention discloses the compounds of formula (I) for use as a medicine as well as the use of these compounds of formula (I) for the manufacture of a medicament for treating one or more of the above mentioned conditions.

The compounds of formula (I), the pharmaceutically acceptable acid addition salts and stereoisomeric forms thereof can have valuable diagnostic properties in that they can be used for detecting or identifying a HDAC in a biological sample comprising detecting or measuring the formation of a complex between a labelled compound and a HDAC.

The detecting or identifying methods can use compounds that are labelled with labelling agents such as radioisotopes, enzymes, fluorescent substances, luminous substances, etc. Examples of the radioisotopes include $^{125}I$, $^{131}I$, $^{3}H$ and $^{14}C$. Enzymes are usually made detectable by conjugation of an appropriate substrate which, in turn catalyses a detectable reaction. Examples thereof include, for example, beta-galactosidase, beta-glucosidase, alkaline phosphatase, peroxidase and malate dehydrogenase, preferably horseradish peroxidase. The luminous substances include, for example, luminol, luminol derivatives, luciferin, aequorin and luciferase.

Biological samples can be defined as body tissue or body fluids. Examples of body fluids are cerebrospinal fluid, blood, plasma, serum, urine, sputum, saliva and the like.

In view of their useful pharmacological properties, the subject compounds may be formulated into various pharmaceutical forms for administration purposes.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those skilled in the art could easily determine the effective amount from the test results presented hereinafter. In general it is contemplated that a therapeutically effective amount would be from 0.05 mg/kg to 100 mg/kg body weight, and in particular from 0.05 mg/kg to 10 mg/kg body weight. It may be appropriate to administer the required dose as two, three, four or more sub-doses at appropriate intervals throughout the day. Said sub-doses may be formulated as unit dosage forms, for example, containing 0.5 to 500 mg, and in particular 10 mg to 500 mg of active ingredient per unit dosage form.

As another aspect of the present invention a combination of a HDAC-inhibitor with another anticancer agent is envisaged, especially for use as a medicine, more specifically in the treatment of cancer or related diseases.

For the treatment of the above conditions, the compounds of the invention may be advantageously employed in combination with one or more other medicinal agents, more particularly, with other anti-cancer agents. Examples of anti-cancer agents are:

platinum coordination compounds for example cisplatin, carboplatin or oxalyplatin;

taxane compounds for example paclitaxel or docetaxel;

topoisomerase I inhibitors such as camptothecin compounds for example irinotecan or topotecan;

topoisomerase II inhibitors such as anti-tumour podophyllotoxin derivatives for example etoposide or teniposide;

anti-tumour vinca alkaloids for example vinblastine, vincristine or vinorelbine;

anti-tumour nucleoside derivatives for example 5-fluorouracil, gemcitabine or capecitabine;

alkylating agents such as nitrogen mustard or nitrosourea for example cyclophosphamide, chlorambucil, carmustine or lomustine;

anti-tumour anthracycline derivatives for example daunorubicin, doxorubicin, idarubicin or mitoxantrone;

HER2 antibodies for example trastuzumab;

estrogen receptor antagonists or selective estrogen receptor modulators for example tamoxifen, toremifene, droloxifene, faslodex or raloxifene;

aromatase inhibitors such as exemestane, anastrozole, letrazole and vorozole;

differentiating agents such as retinoids, vitamin D and retinoic acid metabolism blocking agents (RAMBA) for example accutane;

DNA methyl transferase inhibitors for example azacytidine;

kinase inhibitors for example flavoperidol, imatinib mesylate or gefitinib;

farnesyltransferase inhibitors; or other HDAC inhibitors.

The term "platinum coordination compound" is used herein to denote any tumor cell growth inhibiting platinum coordination compound which provides platinum in the form of an ion.

The term "taxane compounds" indicates a class of compounds having the taxane ring system and related to or derived from extracts from certain species of yew (Taxus) trees.

The term "topisomerase inhibitors" is used to indicate enzymes that are capable of altering DNA topology in eukaryotic cells. They are critical for important cellular functions and cell proliferation. There are two classes of topoisomerases in eukaryotic cells, namely type I and type II. Topoisomerase I is a monomeric enzyme of approximately 100,000 molecular weight. The enzyme binds to DNA and introduces a transient single-strand break, unwinds the double helix (or allows it to unwind) and subsequently reseals the break before dissociating from the DNA strand. Topisomerase II has a similar mechanism of action which involves the induction of DNA strand breaks or the formation of free radicals.

The term "camptothecin compounds" is used to indicate compounds that are related to or derived from the parent camptothecin compound which is a water-insoluble alkaloid derived from the Chinese tree Camptothecin acuminata and the Indian tree Nothapodytes foetida.

The term "podophyllotoxin compounds" is used to indicate compounds that are related to or derived from the parent podophyllotoxin, which is extracted from the mandrake plant.

The term "anti-tumor vinca alkaloids" is used to indicate compounds that are related to or derived from extracts of the periwinkle plant (*Vinca rosea*).

The term "alkylating agents" encompass a diverse group of chemicals that have the common feature that they have the capacity to contribute, under physiological conditions, alkyl groups to biologically vital macromolecules such as DNA. With most of the more important agents such as the nitrogen mustards and the nitrosoureas, the active alkylating moieties are generated in vivo after complex degradative reactions, some of which are enzymatic. The most important pharmacological actions of the alkylating agents are those that disturb the fundamental mechanisms concerned with cell proliferation in particular DNA synthesis and cell division. The capacity of alkylating agents to interfere with DNA function and integrity in rapidly proliferating tissues provides the basis for their therapeutic applications and for many of their toxic properties.

The term "anti-tumour anthracycline derivatives" comprise antibiotics obtained from the fungus *Strep. peuticus* var. *caesius* and their derivatives, characterised by having a tetracycline ring structure with an unusual sugar, daunosamine, attached by a glycosidic linkage.

Amplification of the human epidermal growth factor receptor 2 protein (HER 2) in primary breast carcinomas has been shown to correlate with a poor clinical prognosis for certain patients. Trastuzumab is a highly purified recombinant DNA-derived humanized monoclonal IgG1 kappa antibody that binds with high affinity and specificity to the extracellular domain of the HER2 receptor.

Many breast cancers have estrogen receptors and growth of these tumors can be stimulated by estrogen. The terms "estrogen receptor antagonists" and "selective estrogen receptor modulators" are used to indicate competitive inhibitors of estradiol binding to the estrogen receptor (ER). Selective estrogen receptor modulators, when bound to the ER, induces a change in the three-dimensional shape of the receptor, inhibiting its binding to the estrogen responsive element (ERE) on DNA.

In postmenopausal women, the principal source of circulating estrogen is from conversion of adrenal and ovarian androgens (androstenedione and testosterone) to estrogens (estrone and estradiol) by the aromatase enzyme in peripheral tissues. Estrogen deprivation through aromatase inhibition or inactivation is an effective and selective treatment for some postmenopausal patients with hormone-dependent breast cancer.

The term "antiestrogen agent" is used herein to include not only estrogen receptor antagonists and selective estrogen receptor modulators but also aromatase inhibitors as discussed above.

The term "differentiating agents" encompass compounds that can, in various ways, inhibit cell proliferation and induce differentiation. Vitamin D and retinoids are known to play a major role in regulating growth and differentiation of a wide variety of normal and malignant cell types. Retinoic acid metabolism blocking agents (RAMBA's) increase the levels of endogenous retinoic acids by inhibiting the cytochrome P450-mediated catabolism of retinoic acids.

DNA methylation changes are among the most common abnormalities in human neoplasia. Hypermethylation within the promotors of selected genes is usually associated with inactivation of the involved genes. The term "DNA methyl transferase inhibitors" is used to indicate compounds that act through pharmacological inhibition of DNA methyl transferase and reactivation of tumour suppressor gene expression.

The term "kinase inhibitors" comprises potent inhibitors of kinases that are involved in cell cycle progression and programmed cell death (apoptosis).

The term "farnesyltransferase inhibitors" is used to indicate compounds that were designed to prevent farnesylation of Ras and other intracellular proteins. They have been shown to have effect on malignant cell proliferation and survival.

The term "other HDAC inhibitors" comprises but is not limited to:
short-chain fatty acids for example butyrate, 4-phenylbutyrate or valproic acid;
hydroxamic acids for example suberoylanilide hydroxamic acid (SAHA), biaryl hydroxamate A-161906, bicyclic aryl-N-hydroxycarboxamides, pyroxamide, CG-1521, PXD-101, sulfonamide hydroxamic acid, LAQ-824, trichostatin A (TSA), oxamflatin, scriptaid, m-carboxy cinnamic acid bishydroxamic acid, or trapoxin-hydroxamic acid analogue;
cyclic tetrapeptides for example trapoxin, apidicin or depsipeptide;
benzamides for example MS-275 or CI-994, or
depudecin.

For the treatment of cancer the compounds according to the present invention may be administered to a patient as described above, in conjunction with irradiation. Irradiation means ionising radiation and in particular gamma radiation, especially that emitted by linear accelerators or by radionuclides that are in common use today. The irradiation of the tumour by radionuclides can be external or internal.

The present invention also relates to a combination according to the invention of an anti-cancer agent and a HDAC inhibitor according to the invention.

The present invention also relates to a combination according to the invention for use in medical therapy for example for inhibiting the growth of tumour cells.

The present invention also relates to a combinations according to the invention for inhibiting the growth of tumour cells.

The present invention also relates to a method of inhibiting the growth of tumour cells in a human subject which comprises administering to the subject an effective amount of a combination according to the invention.

This invention further provides a method for inhibiting the abnormal growth of cells, including transformed cells, by administering an effective amount of a combination according to the invention.

The other medicinal agent and HDAC inhibitor may be administered simultaneously (e.g. in separate or unitary compositions) or sequentially in either order. In the latter case, the two compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and HDAC inhibitor being administered, their route of administration, the particular tumour being treated and the particular host being treated. The optimum method and order of administration and the dosage amounts and regime can be readily determined by those skilled in the art using conventional methods and in view of the information set out herein.

The platinum coordination compound is advantageously administered in a dosage of 1 to 500 mg per square meter ($mg/m^2$) of body surface area, for example 50 to 400 $mg/m^2$, particularly for cisplatin in a dosage of about 75 $mg/m^2$ and for carboplatin in about 300 $mg/m^2$ per course of treatment.

The taxane compound is advantageously administered in a dosage of 50 to 400 mg per square meter (mg/m²) of body surface area, for example 75 to 250 mg/m², particularly for paclitaxel in a dosage of about 175 to 250 mg/m² and for docetaxel in about 75 to 150 mg/m² per course of treatment.

The camptothecin compound is advantageously administered in a dosage of 0.1 to 400 mg per square meter (mg/m²) of body surface area, for example 1 to 300 mg/m², particularly for irinotecan in a dosage of about 100 to 350 mg/m² and for topotecan in about 1 to 2 mg/m² per course of treatment.

The anti-tumor podophyllotoxin derivative is advantageously administered in a dosage of 30 to 300 mg per square meter (mg/m²) of body surface area, for example 50 to 250 mg/m², particularly for etoposide in a dosage of about 35 to 100 mg/m² and for teniposide in about 50 to 250 mg/m² per course of treatment.

The anti-tumor vinca alkaloid is advantageously administered in a dosage of 2 to 30 mg per square meter (mg/m²) of body surface area, particularly for vinblastine in a dosage of about 3 to 12 mg/m², for vincristine in a dosage of about 1 to 2 mg/m², and for vinorelbine in dosage of about 10 to 30 mg/m² per course of treatment.

The anti-tumor nucleoside derivative is advantageously administered in a dosage of 200 to 2500 mg per square meter (mg/m²) of body surface area, for example 700 to 1500 mg/m², particularly for 5-FU in a dosage of 200 to 500 mg/m², for gemcitabine in a dosage of about 800 to 1200 mg/m² and for capecitabine in about 1000 to 2500 mg/m² per course of treatment.

The alkylating agents such as nitrogen mustard or nitrosourea is advantageously administered in a dosage of 100 to 500 mg per square meter (mg/m²) of body surface area, for example 120 to 200 mg/m², particularly for cyclophosphamide in a dosage of about 100 to 500 mg/m², for chlorambucil in a dosage of about 0.1 to 0.2 mg/kg, for carmustine in a dosage of about 150 to 200 mg/m², and for lomustine in a dosage of about 100 to 150 mg/m² per course of treatment.

The anti-tumor anthracycline derivative is advantageously administered in a dosage of 10 to 75 mg per square meter (mg/m²) of body surface area, for example 15 to 60 mg/m², particularly for doxorubicin in a dosage of about 40 to 75 mg/m², for daunorubicin in a dosage of about 25 to 45 mg/m², and for idarubicin in a dosage of about 10 to 15 mg/m² per course of treatment.

Trastuzumab is advantageously administered in a dosage of 1 to 5 mg per square meter (mg/m²) of body surface area, particularly 2 to 4 mg/m² per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

These dosages may be administered for example once, twice or more per course of treatment, which may be repeated for example every 7, 14, 21 or 28 days.

In view of their useful pharmacological properties, the components of the combinations according to the invention, i.e. the other medicinal agent and the HDAC inhibitor may be formulated into various pharmaceutical forms for administration purposes. The components may be formulated separately in individual pharmaceutical compositions or in a unitary pharmaceutical composition containing both components.

The present invention therefore also relates to a pharmaceutical composition comprising the other medicinal agent and the HDAC inhibitor together with one or more pharmaceutical carriers.

The present invention also relates to a combination according to the invention in the form of a pharmaceutical composition comprising an anti-cancer agent and a HDAC inhibitor according to the invention together with one or more pharmaceutical carriers.

The present invention further relates to the use of a combination according to the invention in the manufacture of a pharmaceutical composition for inhibiting the growth of tumour cells.

The present invention further relates to a product containing as first active ingredient a HDAC inhibitor according to the invention and as second active ingredient an anticancer agent, as a combined preparation for simultaneous, separate or sequential use in the treatment of patients suffering from cancer.

EXPERIMENTAL PART

The following examples are provided for purposes of illustration.

Hereinafter "DCM" means dichloromethane, "DMA" means dimethylacetamide, "DMF" means dimethylformamide, "EtOAc" means ethyl acetate, "iPrOH" means isopropyl, "MeOH" means methanol, "EtOAc" means ethyl acetate, "EtOH" means ethanol, "TEA" means triethylamine, "TFA" means trifluoroacetic acid and "THF" means tetrahydrofuran.

A. Preparation of the Intermediates

Example A1 a) Preparation of Intermediate 1

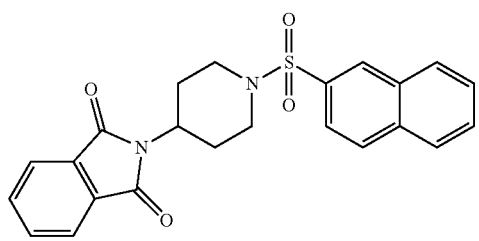 [SMILES: O=C1c2ccccc2C(=O)N1C1CCN(S(=O)(=O)c2ccc3ccccc3c2)CC1]

A solution of 2-naphthalenesulfonyl chloride (0.0094 mol) in DCM (10 ml) was added at 5° C. to a mixture of 2-(4-piperidinyl)-1H-isoindole-1,3(2H)-dione (0.0078 mol) and TEA (0.0109 mol) in DCM (20 ml) under $N_2$ flow. The mixture was kept at room temperature for a week-end. Potassium carbonate 10% was added. The mixture was extracted with DCM. The organic layer was separated, dried (MgSO$_4$), filtered, and the solvent was evaporated till dryness, yielding 3.3 g (100%) of intermediate 1.

b) Preparation of Intermediate 2

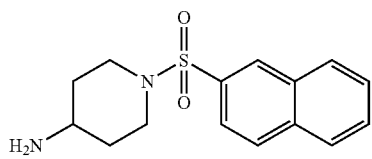 [SMILES: NC1CCN(S(=O)(=O)c2ccc3ccccc3c2)CC1]

A mixture of intermediate 1 (0.0078 mol) in hydrazine monohydrate (3.5 ml) and EtOH (35 ml) was stirred and refluxed for 1 hour. Satured sodium chloride was added. The mixture was extracted with DCM. The organic layer was separated, dried (MgSO$_4$), filtered, and the solvent was evaporated till dryness, yielding 2 g (92%) of intermediate 2, melting point 135° C.

c) Preparation of Intermediate 3

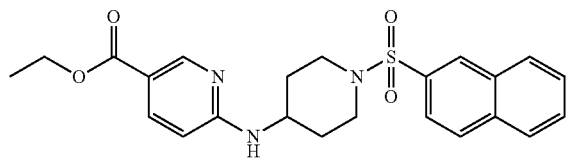 [SMILES: CCOC(=O)c1ccc(NC2CCN(S(=O)(=O)c3ccc4ccccc4c3)CC2)nc1]

A mixture of intermediate 2 (0.0036 mol), 6-chloro-3-pyridinecarboxylic acid, ethyl ester (0.0043 mol) and sodium carbonate (0.0054 ml) in DMA (10 ml) was stirred at 130° C. for 18 hours, poured out into water and extracted with DCM. The organic layer was separated, dried (MgSO$_4$), filtered, and the solvent was evaporated till dryness. The residue (2.5 g) was purified by column chromatography over silica gel (15-40 μm) (eluent: DCM/MeOH 99.5/0.5;). The pure fractions were collected and the solvent was evaporated. The residue (0.68 g, 43%) was crystallized from diethyl ether. The precipitate was filtered off and dried, yielding 0.477 g (30%) of intermediate 3, melting point 215° C.

Example A2 a) Preparation of Intermediate 4

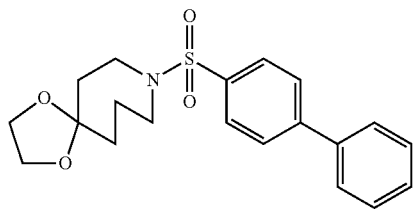 [SMILES: O=S(=O)(c1ccc(-c2ccccc2)cc1)N1CCCC2(CC1)OCCO2]

TEA (0.0112 mol) then a solution of [1,1'-biphenyl]-4-sulfonyl chloride (0.0112 mol) in DCM (5 ml) were added at 5° C. to a mixture of 1,4-dioxa-8-azaspiro[4.6]undecane (0.01 mol) in DCM (10 ml) under N$_2$ flow. The mixture was stirred at room temperature for 18 hours. Potassium carbonate 10% was added. The mixture was extracted with DCM. The organic layer was separated, dried (MgSO$_4$), filtered, and the solvent was evaporated till dryness, yielding 5.1 g (>100%) of intermediate 4.

b) Preparation of Intermediate 5

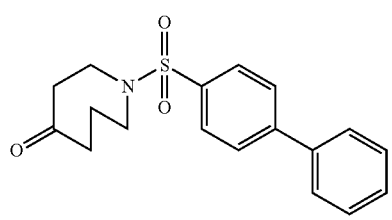 [SMILES: O=C1CCCN(S(=O)(=O)c2ccc(-c3ccccc3)cc2)CC1]

A mixture of intermediate 4 (0.01 mol) in HCl 3N (40 ml) and MeOH (20 ml) was stirred and refluxed, then cooled, poured out on ice, basified with NH$_4$OH conc. and extracted with DCM. The organic layer was separated, dried (MgSO$_4$), filtered, and the solvent was evaporated till dryness, yielding 3.4 g (100%) of intermediate 5.

c) Preparation of Intermediate 6

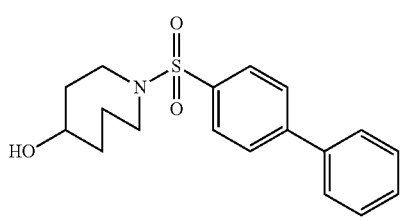 [SMILES: O=S(=O)(c1ccc(-c2ccccc2)cc1)N1CCCC(O)CC1]

Sodium hydroborate (0.011 mol) was added portionwise at 5° C. to a mixture of intermediate 5 (0.01 mol) in MeOH (35 ml) under N$_2$ flow. The mixture was kept at room temperature for 1 hour, poured out into water and extracted with DCM. The organic layer was separated, dried (MgSO$_4$), filtered, and the solvent was evaporated till dryness, yielding 3.2 g (97%) of intermediate 6.

d) Preparation of Intermediate 7

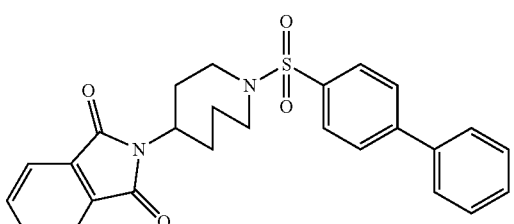

Diazenedicarboxylic acid, bis(1-methylethyl) ester (0.0126 mol) was added dropwise to a mixture of intermediate 6 (0.0096 mol), 1H-isoindole-1,3(2H)-dione (0.0126 mol) and triphenyl-phosphine (0.0126 mol) in THF (35 ml) under N$_2$ flow. The mixture was kept at room temperature for 18 hours. Potassium carbonate 10% was added. The mixture was extracted with DCM. The organic layer was separated, dried (MgSO$_4$), filtered, and the solvent was evaporated till dryness. The residue (13.1 g) was purified by column chromatography over silica gel (15-40 μm) (eluent: DCM/EtOAc 99/1). The pure fractions were collected and the solvent was evaporated, yielding 2.9 g (66%) of intermediate 7.

e) Preparation of Intermediate 8

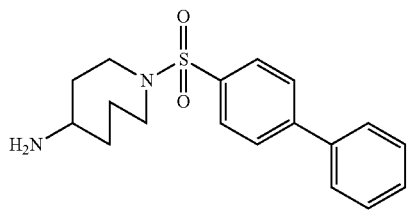 [SMILES: NC1CCCN(S(=O)(=O)c2ccc(-c3ccccc3)cc2)CC1]

A mixture of intermediate 7 (0.0063 mol) in hydrazine monohydrobromide (2.9 ml) and EtOH (30 ml) was stirred and refluxed for 1 hour, then cooled. Satured NaCl was added. The mixture was extracted with DCM. The organic layer was separated, dried (MgSO$_4$), filtered, and the solvent was evaporated till dryness. The residue (2.5 g) was crystallized from acetonitrile/diethyl ether. The precipitate was filtered off and dried, yielding 0.89 g (89%) of intermediate 8, melting point 141° C.

Preparation of Intermediate 19

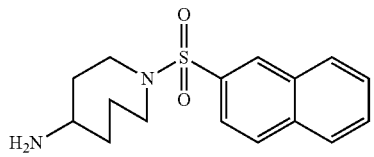 [SMILES: NC1CCCN(S(=O)(=O)c2ccc3ccccc3c2)CC1]

Intermediate 10 was handled analogously as described in example A2 (c, d, e) to give 0.157 g (52%) of intermediate 19, melting point 123° C.

Example A3 a) Preparation of Intermediate 9

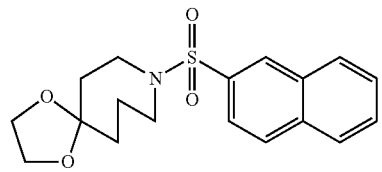 [SMILES: O=S(=O)(c1ccc2ccccc2c1)N1CCCC2(CC1)OCCO2]

TEA (0.0112 mol) then a solution of 2-naphthalenesulfonyl chloride (0.0112 mol) in DCM (5 ml) were added at 5° C. to a mixture of 1,4-dioxa-8-azaspiro[4.6]undecane (0.01 mol) in DCM (10 ml) under N$_2$ flow. The mixture was stirred at room temperature for 18 hours. Potassium carbonate 10% was added. The mixture was extracted with DCM. The organic layer was separated, dried (MgSO$_4$), filtered, and the solvent was evaporated till dryness, yielding 3.9 g (>100%) of intermediate 9.

b) Preparation of Intermediate 10

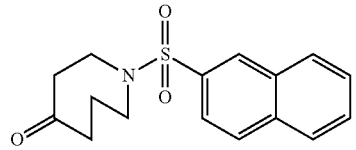 [SMILES: O=C1CCCN(S(=O)(=O)c2ccc3ccccc3c2)CC1]

A mixture of intermediate 9 (0.01 mol) in hydrochloric acid (35 ml) and MeOH (35 ml) was stirred and refluxed for 30 minutes, poured out on ice, basified with NH$_4$OH and extracted with DCM. The organic layer was separated, dried (MgSO$_4$), filtered, and the solvent was evaporated till dryness, yielding 3.4 g (>100%) of intermediate 10.

c) Preparation of Intermediate 11

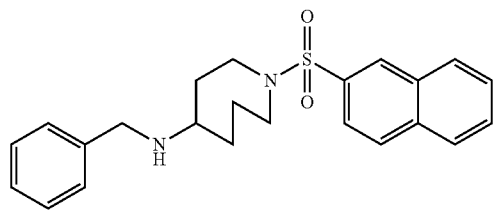 [SMILES: O=S(=O)(c1ccc2ccccc2c1)N1CCCC(NCc2ccccc2)CC1]

Tetraisopropanolatotitanium (0.012 mol) was added at room temperature to a mixture of intermediate 10 (0.01 mol) and benzenemethanamine (0.011 mol) in EtOH (40 ml). The mixture was stirred for 18 hours. Sodium hydroborate (0.011 mol) was added portionwise. The mixture was stirred at room temperature for 1 hour and 30 minutes. Potassium carbonate 10% was added. The mixture was extracted with DCM. The salts were filtered and washed with DCM. The organic layer was separated, dried (MgSO$_4$), filtered, and the solvent was evaporated till dryness, yielding 2.7 g (70%) of intermediate 11.

d) Preparation of Intermediate 12

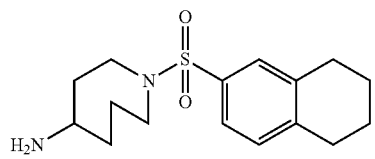 [SMILES: NC1CCCN(S(=O)(=O)c2ccc3c(c2)CCCC3)CC1]

A mixture of intermediate 11 (0.0068 mol) and Pd/C 10% (0.5 g) in acetic acid (3 ml) and MeOH (30 ml) was hydrogenated at 50° C. for 48 hours under a 3 bar pressure, then filtered and washed with DCM. The filtrate was evaporated, yielding: 2.55 g (>100%) of intermediate 12.

Example A4 a) Preparation of Intermediate 13

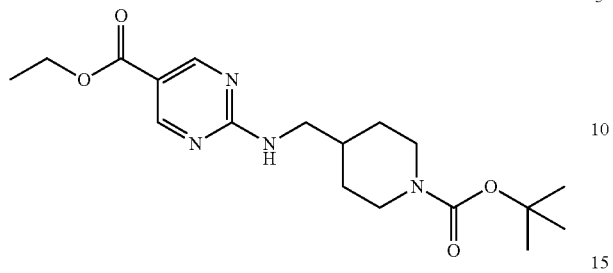

Sodium hydride 60% (0.008 mol) was added portionwise at 0° C. to a mixture of 4-(aminomethyl)-1-piperidinecarboxylic acid, 1,1-dimethylethyl ester (0.004 mol) in THF (20 ml) under $N_2$ flow. The mixture was stirred at 0° C. for 1 hour. A solution of 2-(methylsulfonyl)-5-pyrimidinecarboxylic acid, ethyl ester (0.0052 mol) in THF (10 ml) was added dropwise at 0° C. The mixture was brought to room temperature, stirred for 2 hours, poured out into ice water and extracted with EtOAc. The organic layer was separated, dried ($MgSO_4$), filtered, and the solvent was evaporated. The residue (1.5 g) was purified by column chromatography over silica gel (15-40 µm) (eluent: DCM/MeOH/$NH_4OH$ 98/2/0.1). The pure fractions were collected and the solvent was evaporated. The residue (0.5 g, 35%) was crystallized from DIPE. The precipitate was filtered off and dried, yielding 0.28 g of intermediate 13, melting point 110° C.

b) Preparation of Intermediate 14

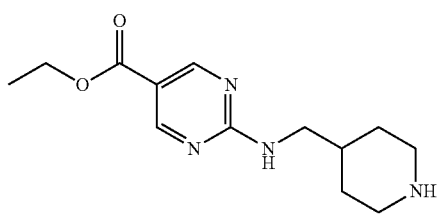 [SMILES: CCOC(=O)c1cnc(NCC2CCNCC2)nc1]

A mixture of intermediate 13 (0.016 mol) in hydrochloric acid 3N (60 ml) and THF (15 ml) was stirred at 80° C. for 6 hours, poured out into ice water, basified with $NH_4OH$ and extracted with DCM. The organic layer was separated, dried ($MgSO_4$), filtered, and the solvent was evaporated, yielding 1.4 g (33%) of intermediate 14.

Example A5 a) Preparation of Intermediate 15

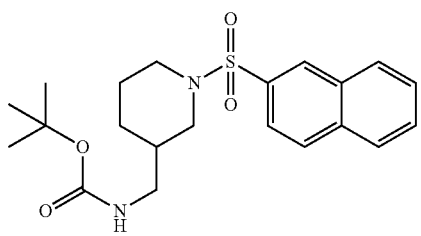 [SMILES: CC(C)(C)OC(=O)NCC1CCCN(S(=O)(=O)c2ccc3ccccc3c2)C1]

A solution of 1-hydroxy-1H-benzotriazole (0.011 mol) in DCM (5 ml) was added at 5° C. to a mixture of (3-piperidinylmethyl)-carbamic acid, 1,1-dimethylethyl ester (0.01 mol) and TEA (0.014 mol) in DCM (5 ml) under $N_2$ flow. The mixture was stirred at room temperature for 18 hours. Water was added. The mixture was extracted with DCM. The organic layer was separated, dried ($MgSO_4$), filtered, and the solvent was evaporated till dryness, yielding 4 g (100%) of intermediate 15.

b) Preparation of Intermediate 16

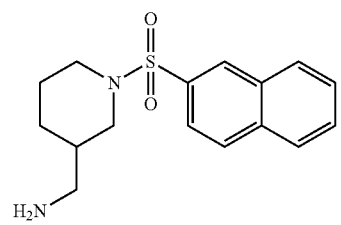

A mixture of intermediate 15 (0.01 mol) in HCl/2-propanol (50 ml) was stirred at 50° C. for 15 minutes, basified with $NH_4OH$ concentrated and the solvent was evaporated till dryness. The residue was taken up in DCM and filtered. The filtrate was dried ($MgSO_4$), filtered and the solvent was evaporated till dryness, yielding 0.53 g (18%) of intermediate 16.

Example A6 a) Preparation of Intermediate 17

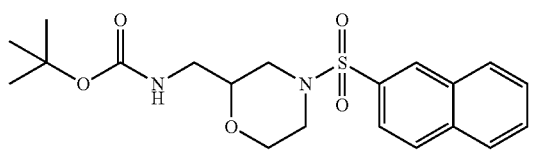 [SMILES: CC(C)(C)OC(=O)NCC1CN(S(=O)(=O)c2ccc3ccccc3c2)CCO1]

Sodium hydride 60% (0.014 mol) was added portionwise at 0° C. to a mixture of (2-morpholinylmethyl)-carbamic acid, 1,1-dimethylethyl ester (0.0092 mol) in THF (30 ml) under $N_2$ flow. The mixture was stirred at 0° C. for 1 hour. A solution of 2-naphthalenesulfonyl chloride (0.0111 mol) in THF (30 ml) was added. The mixture was brought to room temperature overnight, poured out into ice water and extracted with EtOAc. The organic layer was separated, dried ($MgSO_4$), filtered, and the solvent was evaporated. The residue (4.9 g) was purified by column chromatography over silica gel (15-40 µm) (eluent: cyclohexane/EtOAc 70/30). The pure fractions were collected and the solvent was evaporated, yielding 2.15 g (58%) of intermediate 17.

b) Preparation of Intermediate 18

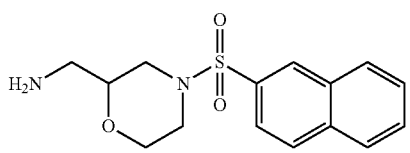 [SMILES: NCC1CN(S(=O)(=O)c2ccc3ccccc3c2)CCO1]

A mixture of intermediate 17 (0.0052 mol) in HCl 6N (25 ml) was stirred at 80° C. for 12 hours, poured out on ice, basified with sodium hydroxide and extracted with DCM. The organic layer was separated, dried (MgSO$_4$), filtered, and the solvent was evaporated, yielding 1 g (63%) of intermediate 18.

B. Preparation of the Final Compounds

Example B1 a) Preparation of Intermediate 20

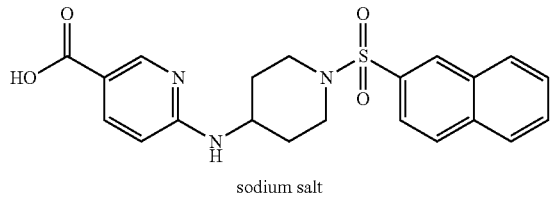 [SMILES: O=C(O)c1ccc(NC2CCN(S(=O)(=O)c3ccc4ccccc4c3)CC2)nc1]

sodium salt

A mixture of intermediate 3 (0.0014 mol) and sodium hydroxide (0.0028 mol) in EtOH (10 ml) was stirred and refluxed for 2 hours, then cooled. The precipitate was filtered, washed with EtOH, then with diethyl ether and dried, yielding 0.5 g (82%) of intermediate 20.

b) Preparation of Intermediate 21

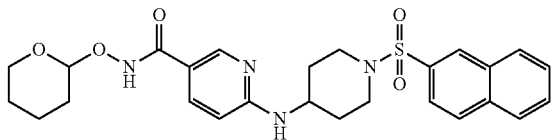 [SMILES: O=C(NOC1CCCCO1)c1ccc(NC2CCN(S(=O)(=O)c3ccc4ccccc4c3)CC2)nc1]

N'-(ethylcarbonimidoyl)-N,N-dimethyl-1,3-propanediamine, monohydrochloride (0.0013 mol) was added to a mixture of intermediate 20 (0.0011 mol), O-(tetrahydro-2H-pyran-2-yl)-hydroxylamine (0.0013 mol) and 1-hydroxy-1H-benzotriazole (0.0013 mol) in DCM/THF (10 ml) under N$_2$ flow. The mixture was stirred at room temperature overnight. Potassium carbonate 10% was added. The mixture was extracted with DCM. The organic layer was separated, dried (MgSO$_4$), filtered, and the solvent was evaporated till dryness. The residue (0.95 g) was purified by column chromatography over silica gel (15-40 μm)(eluent: DCM/MeOH/NH$_4$OH 97/3/0.2). The pure fractions were collected and the solvent was evaporated. The residue (0.48 g, 82%) was crystallized from acetonitile/diethyl ether. The precipitate was filtered off and dried, yielding 0.455 g (77%) of intermediate 21, melting point 129° C.

c) Preparation of compound 1

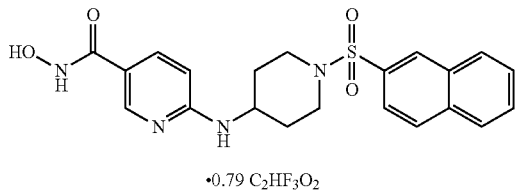

•0.79 C$_2$HF$_3$O$_2$

Trifluoroacetic acid (0.5 ml) was added to a mixture of intermediate 21 (0.0007 mol) in MeOH (5 ml). The mixture was stirred at room temperature for 18 hours. Trifluoroacetic acid (0.5 ml) was added. The mixture was stirred at room temperature for 18 hours. The solvent was evaporated till dryness. The residue was crystallized from MeOH/DCM/diethyl ether. The precipitate was filtered off and dried, yielding 0.195 g (48%) of compound 1 .0.79C$_2$HF$_3$O$_2$, melting point 160° C.

Example B2

Preparation of Intermediate 22

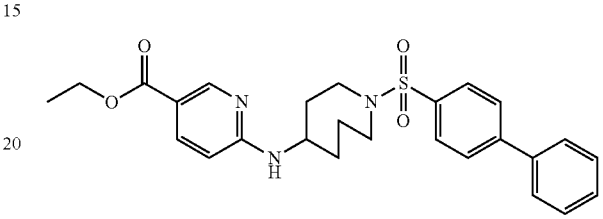

A mixture of intermediate 8 (0.0031 mol), 6-chloro-3-pyridinecarboxylic acid, ethyl ester (0.0037 mol) and sodium carbonate (0.0046 mol) in DMA (10 ml) was stirred at 130° C. for 18 hours. Water was added. The mixture was extracted several times with EtOAc. The organic layer was separated, dried (MgSO$_4$), filtered, and the solvent was evaporated till dryness. The residue (2.1 g) was purified by column chromatography over silica gel (15-40 μm) (eluent: DCM/MeOH 99/1). The pure fractions were collected and the solvent was evaporated. The residue (0.414 g, 28%) was crystallized from diethyl ether. The precipitate was filtered off and dried, yielding 0.294 g (20%) of intermediate 22, melting point 176° C.

Intermediate 22 was handled analogously as described in example [B1] to give 0.084 g (61%) of compound 2 .1.2H$_2$O.0.71C$_2$HF$_3$O$_2$ (1:1), melting point 115° C.

compound 2

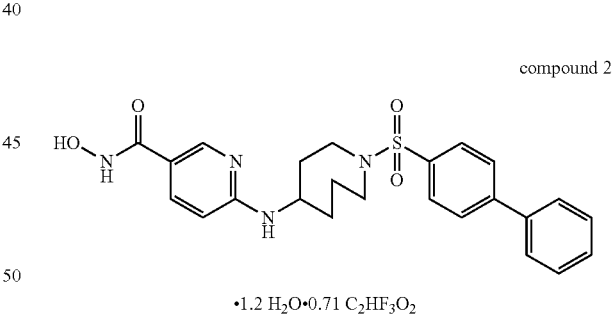

•1.2 H$_2$O•0.71 C$_2$HF$_3$O$_2$

Example B3

Preparation of Intermediate 23

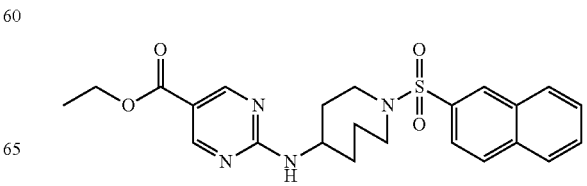

Sodium hydride 60% in oil (0.0045 mol) was added at 5° C. to a mixture of intermediate 19 (0.003 mol) in THF (20 ml) under N₂ flow. The mixture was kept for 1 hour. A solution of 2-(methylsulfonyl)-5-pyrimidinecarboxylic acid, ethyl ester (0.0039 mol) in THF (10 ml) was added. The mixture was stirred at 5° C. for 2 hours. Water was added. The mixture was extracted twice with DCM. The organic layer was separated, dried (MgSO₄), filtered, and the solvent was evaporated till dryness. The residue (1.5 g) was purified by column chromatography over silica gel (15-40 μm) (eluent: DCM/MeOH 99/1). The pure fractions were collected and the solvent was evaporated. The residue (0.47 g, 34%) was crystallized from diethyl ether. The precipitate was filtered off and dried, yielding 0.224 g (16%) of intermediate 23, melting point 186° C.

Intermediate 23 was handled analogously as described in example [B1] to give 0.032 g (26%) of compound 3 .0.22C₂HF₃O₂, melting point 140° C.

compound 3

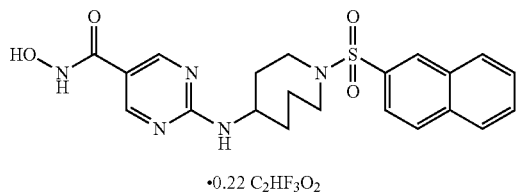

•0.22 C₂HF₃O₂

Example B4

Preparation of Intermediate 24

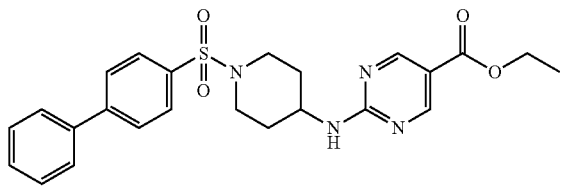 [SMILES: CCOC(=O)c1cnc(NC2CCN(S(=O)(=O)c3ccc(-c4ccccc4)cc3)CC2)nc1]

Sodium hydride (0.0038 mol) was added at 5° C. to a mixture of intermediate 8 (0.0025 mol) in THF (20 ml) under N₂ flow. The mixture was kept for 1 hour. A solution of 2-(methylsulfonyl)-5-pyrimidinecarboxylic acid, ethyl ester (0.0033 mol) in THF (10 ml) was added. The mixture was stirred at 5° C. for 18 hours. Water was added. The mixture was extracted with DCM. The organic layer was separated, dried (MgSO₄), filtered, and the solvent was evaporated till dryness. The residue (1.1 g) was purified by column chromatography over silica gel (15-35 μm) (eluent: cyclohexane/EtOAc 70/30). The pure fractions were collected and the solvent was evaporated. The residue (0.18 g, 15%) was crystallized from diethyl ether. The precipitate was filtered off and dried, yielding 0.141 g (12%) of intermediate 24, melting point 151° C.

Intermediate 24 was handled analogously as described in example [B1] to give 0.04 g (57%) of compound 4 .C₂HF₃O₂, melting point 227° C.

compound 4

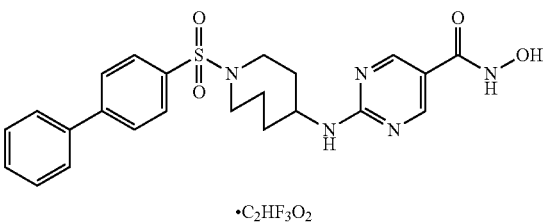

•C₂HF₃O₂

Example B5

Preparation of Intermediate 25

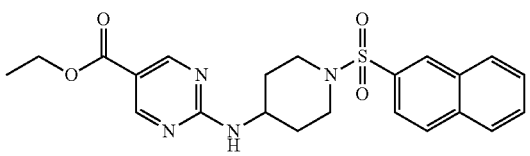

Sodium hydride 60% in oil (0.0045 mol) was added at 5° C. to a mixture of intermediate 2 (0.003 mol) in THF (15 ml) under N₂ flow. The mixture was kept for 1 hour. A solution of 2-(methylsulfonyl)-5-pyrimidinecarboxylic acid, ethyl ester (0.0039 mol) in THF (10 ml) was added. The mixture was stirred at 5° C. for 2 hours. Water was added. The mixture was extracted twice with DCM. The organic layer was separated, dried (MgSO₄), filtered, and the solvent was evaporated till dryness. The residue (1.4 g) was purified by column chromatography over silica gel (15-40 μm) (eluent: DCM/MeOH 99/1). The pure fractions were collected and the solvent was evaporated. The residue (0.49 g, 37%) was crystallized from acetonitrile. The precipitate was filtered, washed with diethyl ether and dried, yielding 0.172 g (13%) of intermediate 25, melting point 226° C.

Intermediate 25 was handled analogously as described in example [B1] to give 0.064 g (49%) of compound 5 .0.17C₂HF₃O₂, melting point 256° C.

compound 5

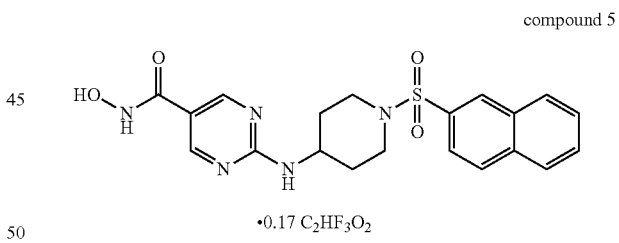

•0.17 C₂HF₃O₂

Example B6

Preparation of Intermediate 26

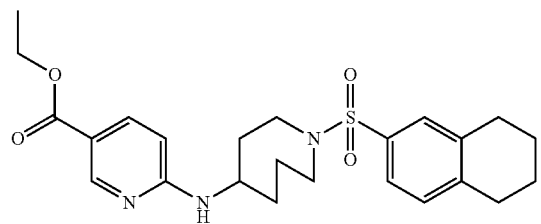 [SMILES: CCOC(=O)c1ccc(NC2CCCN(S(=O)(=O)c3ccc4c(c3)CCCC4)CC2)nc1]

A mixture of intermediate 12 (0.0052 mol), 6-chloro-3-pyridinecarboxylic acid, ethyl ester (0.0062 mol) and sodium carbonate (0.0078 mol) in DMA (20 ml) was stirred at 130° C. for 18 hours. Water was added. The mixture was extracted with EtOAc. The organic layer was separated, dried (MgSO$_4$), filtered, and the solvent was evaporated till dryness. The residue (2.6 g) was purified by column chromatography over silica gel 915-40 µm) (eluent: DCM/MeOH 99/1;). The pure fractions were collected and the solvent was evaporated, yielding 0.64 g (27%) of intermediate 26, melting point 146° C. Intermediate 26 was handled analogously as described in example [B1] to give 0.263 g (67%) of compound 6 H$_2$O (1:1).0.73C$_2$HF$_3$O$_2$, melting point 115° C.

compound 6

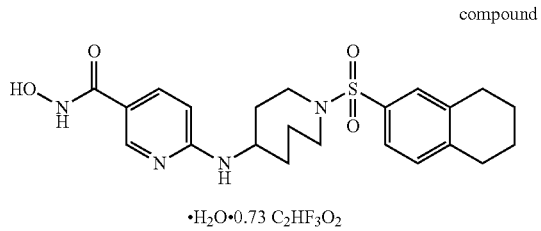

·H$_2$O·0.73 C$_2$HF$_3$O$_2$

Example B7 b) Preparation of Intermediate 27

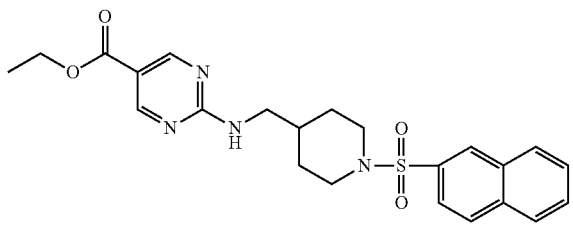 [SMILES: CCOC(=O)c1cnc(NCC2CCN(S(=O)(=O)c3ccc4ccccc4c3)CC2)nc1]

A solution of 2-naphthalenesulfonyl chloride (0.0006 mol) in DCM (2 ml) was added dropwise at 0° C. to a mixture of intermediate 14 (0.0005 mol) and TEA (0.0008 mol) in DCM (3 ml). The mixture was stirred at room temperature for 12 hours, poured out into water and extracted with EtOAc. The organic layer was separated, dried (MgSO$_4$), filtered, and the solvent was evaporated. The residue (0.33 g) was purified by column chromatography over silica gel (10 µm) (eluent: DCM 100). The pure fractions were collected and the solvent was evaporated, yielding 0.21 g (80%) of intermediate 27. Intermediate 27 was handled analogously as described in example [B1] to give 0.043 g (33%) of compound 7, melting point 240° C.

compound 7

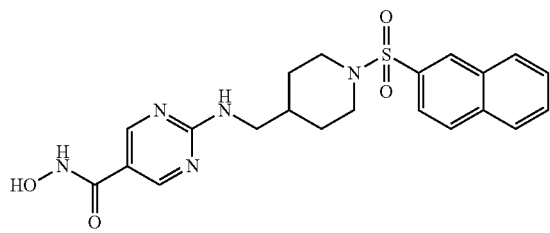

Example B8

Preparation of

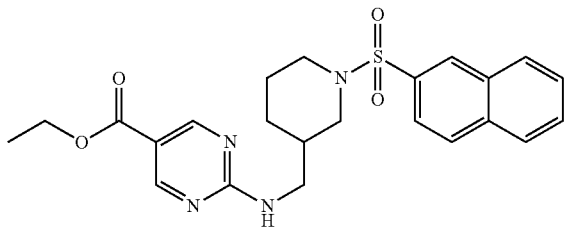 [SMILES: CCOC(=O)c1cnc(NCC2CCCN(S(=O)(=O)c3ccc4ccccc4c3)C2)nc1]

Sodium hydride 60% in oil (0.0023 mol) was added portionwise at 5° C. to a mixture of intermediate 16 (0.0017 mol) in THF (5 ml) under N$_2$ flow. The mixture was stirred for 30 minutes. A solution of 2-(methylsulfonyl)-5-pyrimidinecarboxylic acid, ethyl ester (0.0021 mol) in THF (2 ml) was added. The mixture was stirred at room temperature for 18 hours. Potassium carbonate 10% was added. The mixture was extracted with DCM. The organic layer was separated, dried (MgSO$_4$), filtered, and the solvent was evaporated till dryness. The residue (0.72 g) was purified by column chromatography over silica gel (15-40 µm) (eluent: DCM/MeOH 99/1). The pure fractions were collected and the solvent was evaporated, yielding 0.3 g (39%) of intermediate 28. Intermediate 28 was handled analogously as described in example [B1] to give 0.119 g (75%) of compound 8, melting point 137° C.

compound 8

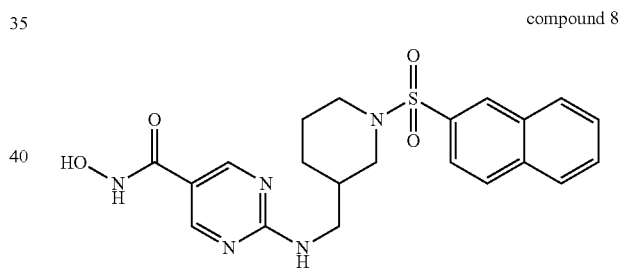

Example B9

Preparation of Intermediate 29

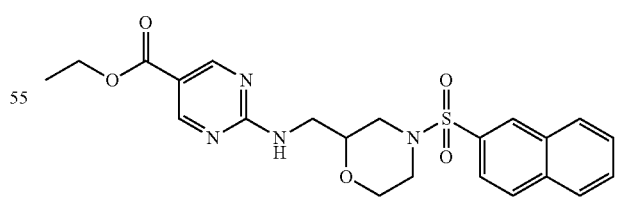

A mixture of intermediate 18 (0.0019 mol), 2-(methylsulfonyl)-5-pyrimidinecarboxylic acid, ethyl ester (0.0025 mol) and potassium carbonate (0.0039 mol) in acetonitrile (15 ml) was stirred at room temperature for 12 hours, poured out into ice water and extracted with EtOAc. The organic layer was washed with water, dried (MgSO$_4$), filtered, and the solvent was evaporated. The residue (1 g) was purified by column chromatography over silica gel (15-40 µm) (eluent: DCM/

EtOAc 80/20). The pure fractions were collected and the solvent was evaporated. The residue (0.48 g, 89%) was crystallized from CH₃CN/diethyl ether. The precipitate was filtered off and dried, yielding 0.2 g of intermediate 29, melting point 168° C. Intermediate 29 was handled analogously as described in example [B1] to give 0.08 g (73%) of compound 9, melting point 226° C.

compound 9

Table F-1 lists the compounds that were prepared according to one of the above Examples. The following abbreviations were used in the tables: .C₂HF₃O₂ stands for the trifluoroacetate salt.

TABLE F-1

•0.79 C₂HF₃O₂; Co. No. 1; Ex. [B1]; mp. 160° C.

•0.83 C₂HF₃O₂; Co. No. 10; Ex. [B1]; mp. 182° C.

0.84 C₂HF₃O₂; Co. No. 11; Ex. [B1]; mp. 188° C.

•1.2 H₂O•0.71 C₂HF₃O₂; Co. No. 2; Ex. [B2]; mp. 115° C.

TABLE F-1-continued

•2 H₂O•0.53 C₂HF₃O₂; Co. No. 12; Ex. [B2]; mp. 147° C.

Co. No. 13; Ex. [B2]; mp. 213° C.

•0.22 C₂HF₃O₂; Co. No. 3; Ex. [B3]; mp. 140° C.

Co. No. 14; Ex. [B3]; mp. 250° C.

•C₂HF₃O₂; Co. No. 4; Ex. [B4]; mp. 227° C.

•0.17 C₂HF₃O₂; Co. No. 5; Ex. [B5]; mp. 256° C.

•H₂O•0.73 C₂HF₃O₂; Co. No. 6; Ex. [B6]; mp. 146° C.

TABLE F-1-continued

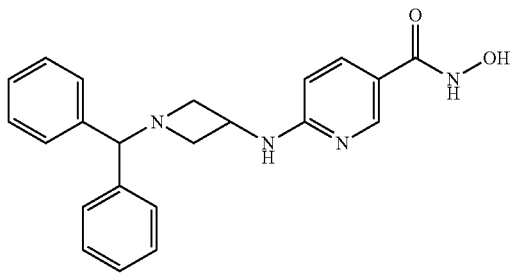

·2.27 C$_2$HF$_3$O$_2$; Co. No. 15; Ex. [B6]; mp. 192° C.

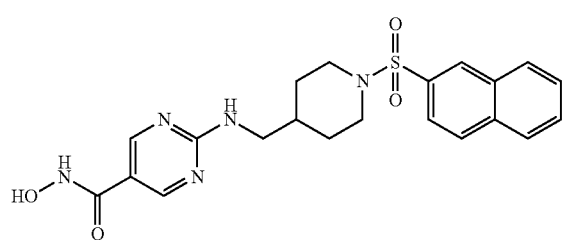

Co. No. 7; Ex. [B7]; mp. 240° C.

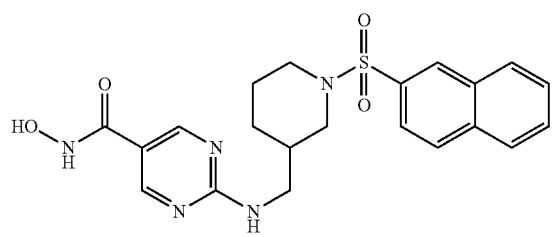

Co. No. 8; Ex. [B8]; mp. 137° C.

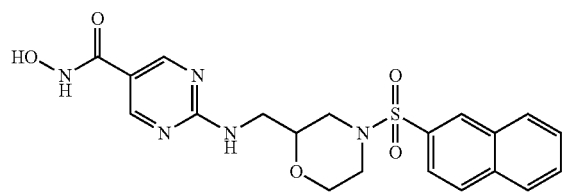

Co. No. 9; Ex. [B9]; mp. 226° C.

C. Pharmacological Example

The in vitro assay for inhibition of histone deacetylase (see example C.1) measures the inhibition of HDAC enzymatic activity obtained with the compounds of formula (I).

Cellular activity of the compounds of formula (I) was determined on A2780 tumour cells using a colorimetric assay for cell toxicity or survival (Mosmann Tim, Journal of Immunological Methods 65: 55-63, 1983)(see example C.2).

Kinetic solubility in aqueous media measures the ability of a compound to stay in aqueous solution upon dilution (see example C.3).

DMSO-stock solutions are diluted with a single aqueous buffer solvent in 3 consecutive steps. For every dilution turbidity is measured with a nephelometer.

Metabolism of drugs means that a lipid-soluble xenobiotic or endobiotic compound is enzymatically transformed into (a) polar, water-soluble, and excretable metabolite(s). The major organ for drug metabolism is the liver. The metabolic products are often less active than the parent drug or inactive. However, some metabolites may have enhanced activity or toxic effects. Thus drug metabolism may include both "detoxication" and "toxication" processes. One of the major enzyme systems that determine the organism's capability of dealing with drugs and chemicals is represented by the cytochrome P450 monooxygenases, which are NADPH dependent enzymes. Metabolic stability of compounds can be determined in vitro with the use of subcellular human tissue (see example C.4). Here metabolic stability of the compounds is expressed as % of drug metabolised after 15 minutes incubation of these compounds with microsomes. Quantitation of the compounds was determined by LC-MS analysis.

The tumour suppressor p53 transcriptionally activates a number of genes including the WAF1/CIP1 gene in response to DNA damage. The 21 kDa product of the WAF1 gene is found in a complex involving cyclins, cyclin dependent kinases (CDKs), and proliferating cell nuclear antigen (PCNA) in normal cells but not transformed cells and appears to be a universal inhibitor of CDK activity. One consequence of p21WAF1 binding to and inhibiting CDKs is to prevent CDK-dependent phosphorylation and subsequent inactivation of the Rb protein, which is essential for cell cycle progression. Induction of p21WAF1 in response to cellular contact with a HDAC inhibitor is therefore a potent and specific indicator of inhibition of cell cycle progression at both the G1 and G2 checkpoints.

The capacity of the compounds to induce p21WAF1 was measured with the p21WAF1 enzyme linked immunosorbent assay (WAF1 ELISA of Oncogene). The p21WAF 1 assay is a "sandwich" enzyme immunoassay employing both mouse monoclonal and rabbit polyclonal antibodies. A rabbit polyclonal antibody, specific for the human WAF1 protein, has been immobilized onto the surface of the plastic wells provided in the kit. Any p21WAF present in the sample to be assayed will bind to the capture antibody. The biotinylated detector monoclonal antibody also recognizes human p21WAF1 protein, and will bind to any p21WAF1, which has been retained by the capture antibody. The detector antibody, in turn, is bond by horseradish peroxidas-conjugated streptavidin. The horseradish peroxidase catalyses the conversion of the chromogenic substrate tetra-methylbenzidine from a colorless solution to a blue solution (or yellow after the addition of stopping reagent), the intensity of which is proportional to the amount of p21WAF1 protein bond to the plate. The colored reaction product is quantified using a spectrophotometer. Quantitation is achieved by the construction of a standard curve using known concentrations of p21WAF1 (provided lyophilised)(see example C.5).

Example C.1

In Vitro Assay for Inhibition of Histone Deacetylase

HeLa nuclear extracts (supplier: Biomol) were incubated at 60 μg/ml with 2×10$^{-8}$ M of radiolabeled peptide substrate. As a substrate for measuring HDAC activity a synthetic peptide, i.e. the amino acids 14-21 of histone H4, was used. The substrate is biotinylated at the NH$_2$-terminal part with a 6-aminohexanoic acid spacer, and is protected at the COOH-terminal part by an amide group and specifically [$^3$H]acetylated at lysine 16. The substrate, biotin-(6-aminohexanoic) Gly-Ala-([$^3$H]-acetyl-Lys-Arg-His-Arg-Lys-Val-NH$_2$), was added in a buffer containing 25 mM Hepes, 1 M sucrose, 0.1 mg/ml BSA and 0.01% Triton X-100 at pH 7.4. After 30 min the deacetylation reaction was terminated by the addition of HCl and acetic acid. (final concentration 0.035 mM and 3.8 mM respectively). After stopping the reaction, the free $^3$H-acetate was extracted with ethylacetate. After mixing and centrifugation, the radioactivity in an aliquot of the upper (organic) phase was counted in a β-counter.

For each experiment, controls (containing HeLa nuclear extract and DMSO without compound), a blank incubation (containing DMSO but no HeLa nuclear extract or compound) and samples (containing compound dissolved in DMSO and HeLa nuclear extract) were run in parallel. In first instance, compounds were tested at a concentration of $10^{-5}$M. When the compounds showed activity at $10^{-5}$M, a concentration-response curve was made wherein the compounds were tested at concentrations between $10^{-5}$M and $10^{-12}$M. In each test the blank value was substracted from both the control and the sample values. The control sample represented 100% of substrate deactylation. For each sample the radioactivity was expressed as a percentage of the mean value of the controls. When appropriate $IC_{50}$-values (concentration of the drug, needed to reduce the amount of metabolites to 50% of the control) were computed using probit analysis for graded data. Herein the effects of test compounds are expressed as $pIC_{50}$ (the negative log value of the $IC_{50}$-value). All tested compounds showed enzymatic activity at a test concentration of $10^{-5}$M and 14 compounds had a $pIC_{50} \geq 5$ (see table F-2).

Example C.2

Determination of Antiproliferative Activity on A2780 Cells

All compounds tested were dissolved in DMSO and further dilutions were made in culture medium. Final DMSO concentrations never exceeded 0.1% (v/v) in cell proliferation assays. Controls contained A2780 cells and DMSO without compound and blanks contained DMSO but no cells. MTT was dissolved at 5 mg/ml in PBS. A glycine buffer comprised of 0.1 M glycine and 0.1 M NaCl buffered to pH 10.5 with NaOH (1 N) was prepared (all reagents were from Merck).

The human A2780 ovarian carcinoma cells (a kind gift from Dr. T. C. Hamilton [Fox Chase Cancer Centre, Pennsylvania, USA]) were cultured in RPMI 1640 medium supplemented with 2 mM L-glutamine, 50 µg/ml gentamicin and 10% fetal calf serum. Cells were routinely kept as monolayer cultures at 37° C. in a humidified 5% $CO_2$ atmosphere. Cells were passaged once a week using a trypsin/EDTA solution at a split ratio of 1:40. All media and supplements were obtained from Life Technologies. Cells were free of mycoplasma contamination as determined using the Gen-Probe Mycoplasma Tissue Culture kit (supplier: BioMérieux).

Cells were seeded in NUNC™ 96-well culture plates (Supplier: Life Technologies) and allowed to adhere to the plastic overnight. Densities used for plating were 1500 cells per well in a total volume of 200 µl medium. After cell adhesion to the plates, medium was changed and drugs and/or solvents were added to a final volume of 200 µl. Following four days of incubation, medium was replaced by 200 µl fresh medium and cell density and viability was assessed using an MTT-based assay. To each well, 25 µl MTT solution was added and the cells were further incubated for 2 hours at 37° C. The medium was then carefully aspirated and the blue MTT-formazan product was solubilized by addition of 25 µl glycine buffer followed by 100 µl of DMSO. The microtest plates were shaken for 10 min on a microplate shaker and the absorbance at 540 nm was measured using an Emax 96-well spectrophotometer (Supplier: Sopachem). Within an experiment, the results for each experimental condition are the mean of 3 replicate wells. For initial screening purposes, compounds were tested at a single fixed concentration of $10^{-6}$ M. For active compounds, the experiments were repeated to establish full concentration-response curves. For each experiment, controls (containing no drug) and a blank incubation (containing no cells or drugs) were run in parallel. The blank value was subtracted from all control and sample values. For each sample, the mean value for cell growth (in absorbance units) was expressed as a percentage of the mean value for cell growth of the control. When appropriate, $IC_{50}$-values (concentration of the drug, needed to reduce cell growth to 50% of the control) were computed using probit analysis for graded data (Finney, D. J., Probit Analyses, $2^{nd}$ Ed. Chapter 10, Graded Responses, Cambridge University Press, Cambridge 1962). Herein the effects of test compounds are expressed as $pIC_{50}$ (the negative log value of the $IC_{50}$-value). Most of the tested compounds showed cellular activity at a test concentration of $10^{-6}$ M and 14 compounds had a $pIC_{50} \geq 5$ (see table F-2).

Example C.3

Kinetic Solubility in Aqueous Media

In the first dilution step, 10 µl of a concentrated stock-solution of the active compound, solubilized in DMSO (5 mM), was added to 100 µl phosphate citrate buffer pH 7.4 and mixed. In the second dilution step, an aliquot (20 µl) of the first dilution step was further dispensed in 100 µl phosphate citrate buffer pH 7.4 and mixed. Finally, in the third dilution step, a sample (20 µl) of the second dilution step was further diluted in 100 µl phosphate citrate buffer pH 7.4 and mixed. All dilutions were performed in 96-well plates. Immediately after the last dilution step the turbidity of the three consecutive dilution steps were measured with a nephelometer. Dilution was done in triplicate for each compound to exclude occasional errors. Based on the turbidity measurements a ranking is performed into 3 classes. Compounds with high solubility obtained a score of 3 and for this compounds the first dilution is clear. Compounds with medium solubility obtained a score of 2. For these compounds the first dilution is unclear and the second dilution is clear. Compounds with low solubility obtained a score of 1 and for these compounds both the first and the second dilution are unclear. The solubility of 14 compounds was measured. From these compounds 6 showed a score of 3, 2 had a score of 2 and 6 demonstrated a score of 1 (see table F-2).

Example C.4

Metabolic Stability

Sub-cellular tissue preparations were made according to Gorrod et al. (Xenobiotica 5: 453-462, 1975) by centrifugal separation after mechanical homogenization of tissue. Liver tissue was rinsed in ice-cold 0.1 M Tris-HCl (pH 7.4) buffer to wash excess blood. Tissue was then blotted dry, weighed and chopped coarsely using surgical scissors. The tissue pieces were homogenized in 3 volumes of ice-cold 0.1 M phosphate buffer (pH 7.4) using either a Potter-S (Braun, Italy) equipped with a Teflon pestle or a Sorvall Omni-Mix homogeniser, for 7×10 sec. In both cases, the vessel was kept in/on ice during the homogenization process.

Tissue homogenates were centrifuged at 9000×g for 20 minutes at 4° C. using a Sorvall centrifuge or Beckman Ultracentrifuge. The resulting supernatant was stored at −80° C. and is designated 'S9'.

The S9 fraction can be further centrifuged at 100.000×g for 60 minutes (4° C.) using a Beckman ultracentrifuge. The resulting supernatant was carefully aspirated, aliquoted and designated 'cytosol'. The pellet was re-suspended in 0.1 M phosphate buffer (pH 7.4) in a final volume of 1 ml per 0.5 g original tissue weight and designated 'microsomes'.

All sub-cellular fractions were aliquoted, immediately frozen in liquid nitrogen and stored at −80° C. until use.

For the samples to be tested, the incubation mixture contained PBS (0.1M), compound (5 µM), microsomes (1 mg/ml) and a NADPH-generating system (0.8 mM glucose-6-phosphate, 0.8 mM magnesium chloride and 0.8 Units of glucose-6-phosphate dehydrogenase). Control samples contained the same material but the microsomes were replaced by heat inactivated (10 mM at 95 degrees Celsius) microsomes. Recovery of the compounds in the control samples was always 100%.

The mixtures were preincubated for 5 mM at 37 degrees Celsius. The reaction was started at timepoint zero (t=0) by addition of 0.8 mM NADP and the samples were incubated for 15 min (t=15). The reaction was terminated by the addition of 2 volumes of DMSO. Then the samples were centrifuged for 10 min at 900×g and the supernatants were stored at room temperature for no longer as 24 h before analysis. All incubations were performed in duplo. Analysis of the supernatants was performed with LC-MS analysis. Elution of the samples was performed on a Xterra MS C18 (50×4.6 mm, 5 µm, Waters, US). An Alliance 2790 (Supplier: Waters, US) HPLC system was used. Elution was with buffer A (25 mM ammoniumacetate (pH 5.2) in H$_2$O/acetonitrile (95/5)), solvent B being acetonitrile and solvent C methanol at a flow rate of 2.4 ml/min. The gradient employed was increasing the organic phase concentration from 0% over 50% B and 50% C in 5 min up to 100% B in 1 min in a linear fashion and organic phase concentration was kept stationary for an additional 1.5 min. Total injection volume of the samples was 25 µl.

A Quattro (supplier: Micromass, Manchester, UK) triple quadrupole mass spectrometer fitted with and ESI source was used as detector. The source and the desolvation temperature were set at 120 and 350° C. respectively and nitrogen was used as nebuliser and drying gas. Data were acquired in positive scan mode (single ion reaction). Cone voltage was set at 10 V and the dwell time was 1 sec.

Metabolic stability was expressed as % metabolism of the compound after 15 min of incubation in the presence of active microsomes $$(E(act))(\% \text{ metabolism} = 100\% - \left(\left(\frac{\text{Total Ion Current}(TIC) \text{ of } E(act) \text{ at } t = 15}{TIC \text{ of } E(act) \text{ at } t = 0}\right) \times 100\right).$$

Compounds that had a percentage metabolism less than 20% were defined as highly metabolic stable. Compound that had a metabolism between 20 and 70% were defined as intermediately stable and compounds that showed a percentage metabolism higher than 70 were defined as low metabolic stable. Three reference compounds were always included whenever a metabolic stability screening was performed. Verapamil was included as a compound with low metabolic stability (% metabolism=73%). Cisapride was included as a compound with medium metabolic stability (% metabolism 45%) and propanol was included as a compound with intermediate to high metabolic stability (25% metabolism). These reference compounds were used to validate the metabolic stability assay.

Three compounds were tested. One compound had a percentage metabolism less than 20% and two compounds had a percentage metabolism between 20 and 70%.

Example C.5 p21 Induction Capacity

The following protocol has been applied to determine the p21 protein expression level in human A2780 ovarian carcinoma cells. The A2780 cells (20000 cells/180 µl) were seeded in 96 microwell plates in RPMI 1640 medium supplemented with 2 mM L-glutamine, 50 µg/ml gentamicin and 10% fetal calf serum. 24 hours before the lysis of the cells, compounds were added at final concentrations of $10^{-5}$, $10^{-6}$, $10^{-7}$ and $10^{-8}$ M. All compounds tested were dissolved in DMSO and further dilutions were made in culture medium. 24 hours after the addition of the compound, the supernatants were removed from the cells. Cells were washed with 200 µl ice-cold PBS. The wells were aspirated and 30 µl of lysisbuffer (50 mM Tris.HCl (pH 7.6), 150 mM NaCl, 1% Nonidet p40 and 10% glycerol) was added. The plates were incubated overnight at −70° C.

The appropriate number of microtiter wells were removed from the foil pouch and placed into an empty well holder. A working solution (1×) of the Wash Buffer (20× plate wash concentrate: 100 ml 20-fold concentrated solution of PBS and surfactant. Contains 2% chloroacetamide) was prepared. The lyophilised p21WAF standard was reconstituted with distilled H$_2$O and further diluted with sample diluent (provided in the kit).

The samples were prepared by diluting them 1:4 in sample diluent. The samples (100 µl) and the p21WAF1 standards (100 µl) were pipetted into the appropriate wells and incubated at room temperature for 2 hours. The wells were washed 3 times with 1× wash buffer and then 100 µl of detector antibody reagent (a solution of biotinylated monoclonal p21WAF1 antibody) was pipetted into each well. The wells were incubated at room temperature for 1 hour and then washed three times with 1× wash buffer. The 400× conjugate (peroxidase streptavidine conjugate: 400-fold concentrated solution) was diluted and 100 µl of the 1× solution was added to the wells. The wells were incubated at room temperature for 30 min and then washed 3 times with 1× wash buffer and 1 time with distilled H$_2$O. Substrate solution (chromogenic substrate)(100 µl) was added to the wells and the wells were incubated for 30 minutes in the dark at room temperature. Stop solution was added to each well in the same order as the previously added substrate solution. The absorbance in each well was measured using a spectrophotometric plate reader at dual wavelengths of 450/595 nm.

For each experiment, controls (containing no drug) and a blank incubation (containing no cells or drugs) were run in parallel. The blank value was substracted from all control and sample values. For each sample, the value for p21WAF1 induction (in absorbance units) was expressed as the percentage of the value for p21WAF1 present in the control. Percentage induction higher than 130% was defined as significant induction. Three compounds were tested in this assay and showed significant induction.

Table F-2: Table F-2 lists the results of the compounds that were tested according to example C.1, C.2, and C.3.

TABLE F-2

Table F-2 listes the results of the compounds that were tested according to example C.1, C.2, and C.3.

| Co. No. | Enzyme activity pIC50 | Cellular activity pIC50 | Solubility Score |
|---|---|---|---|
| 15 | <5 | <5 | 3 |
| 10 | 6.81 | 5.396 | 3 |
| 1 | 7.676 | 5.61 | 3 |
| 3 | 7.306 | 5.506 | 2 |
| 11 | 6.594 | 5.6 | 1 |
| 5 | 7.525 | 5.473 | 3 |
| 4 | 7.314 | 5.838 | 1 |
| 14 | 7.077 | 5.201 | 1 |
| 6 | 6.853 | 5.345 | 2 |
| 12 | 7.592 | 5.718 | 3 |
| 2 | 6.871 | 5.804 | 1 |
| 13 | 6.934 | 5.452 | |
| 7 | 7.408 | 5.109 | 1 |
| 8 | 7.23 | 5.721 | 1 |
| 9 | 7.161 | 5.667 | 3 |

D. Composition Example

Film-Coated Tablets

Preparation of Tablet Core

A mixture of 100 g of a compound of formula (I), 570 g lactose and 200 g starch is mixed well and thereafter humidified with a solution of 5 g sodium dodecyl sulphate and 10 g polyvinyl-pyrrolidone in about 200 ml of water. The wet powder mixture is sieved, dried and sieved again. Then there is added 100 g microcrystalline cellulose and 15 g hydrogenated vegetable oil. The whole is mixed well and compressed into tablets, giving 10.000 tablets, each comprising 10 mg of a compound of formula (I).

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

The invention claimed is:

1. A compound of formula (I), the N-oxide forms, the pharmaceutically acceptable addition salts and the stereo-chemically isomeric forms thereof, wherein n is 1 and m is 1 or n is 0 and m is 2;
t is 0 or 1 and when t is 0 then a direct bond is intended;
Q is C;
X is N;
Y is N;
Z is —$CH_2$—;
$R^1$ is —C(O)$NR^3R^4$, —N(H)C(O)$R^7$, —C(O)—$C_{1-6}$alkanediyl$SR^7$, —$NR^8$C(O)N(OH)$R^7$, —$NR^8$C(O)$C_{1-6}$alkanediyl$SR^7$, or —$NR^8$C(O)C=N(OH)$R^7$ wherein $R^3$ and $R^4$ are each independently hydrogen, hydroxy, $C_{1-6}$alkyl, hydroxy$C_{1-6}$alkyl, amino$C_{1-6}$alkyl or aminoaryl; $R^7$ is hydrogen, $C_{1-6}$alkyl, $C_{1-6}$alkylcarbonyl, $C_{1-6}$alkylpyrazinyl, pyridinone, pyrrolidinone or methylimidazolyl; and $R^8$ is hydrogen or $C_{1-6}$alkyl;
$R^2$ is hydrogen, hydroxy, amino, hydroxy$C_{1-6}$alkyl, $C_{1-6}$alkyl, $C_{1-6}$alkyloxy, aryl$C_{1-6}$alkyl, aminocarbonyl, hydroxycarbonyl, amino$C_{1-6}$alkyl, aminocarbonyl$C_{1-6}$alkyl, hydroxycarbonyl$C_{1-6}$alkyl, hydroxyaminocarbonyl, $C_{1-6}$alkyloxycarbonyl, $C_{1-6}$alkylamino$C_{1-6}$alkyl or di($C_{1-6}$alkyl)amino$C_{1-6}$alkyl;
-L- is a bivalent radical that is $C_{1-6}$alkanediyl, carbonyl, sulfonyl, or $C_{1-6}$alkanediyl substituted with phenyl;

—(A)

is a radical that is

-continued
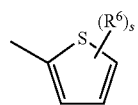 (a-9)
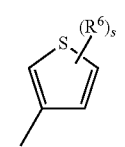 (a-10)
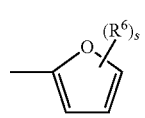 (a-11)
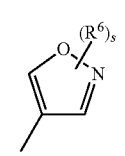 (a-12)
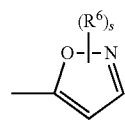 (a-13)
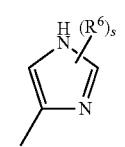 (a-14)
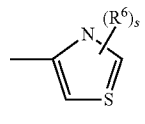 (a-15)
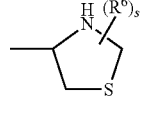 (a-16)
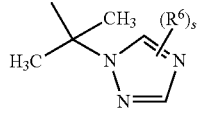 (a-17)
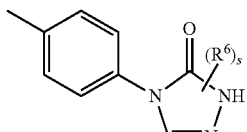 (a-18)
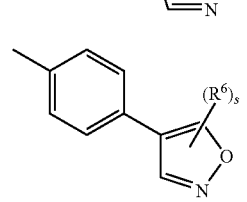 (a-19)
-continued
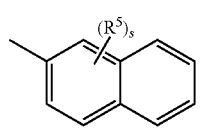 (a-20)
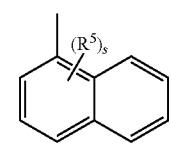 (a-21)
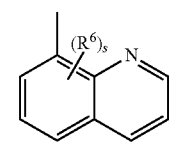 (a-22)
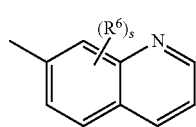 (a-23)
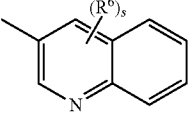 (a-24)
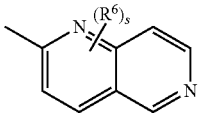 (a-25)
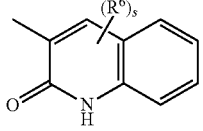 (a-26)
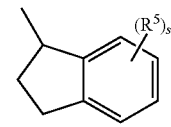 (a-27)
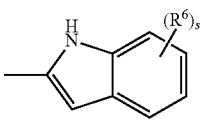 (a-28)
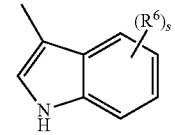 (a-29)
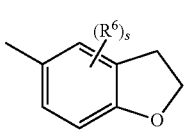 (a-30)

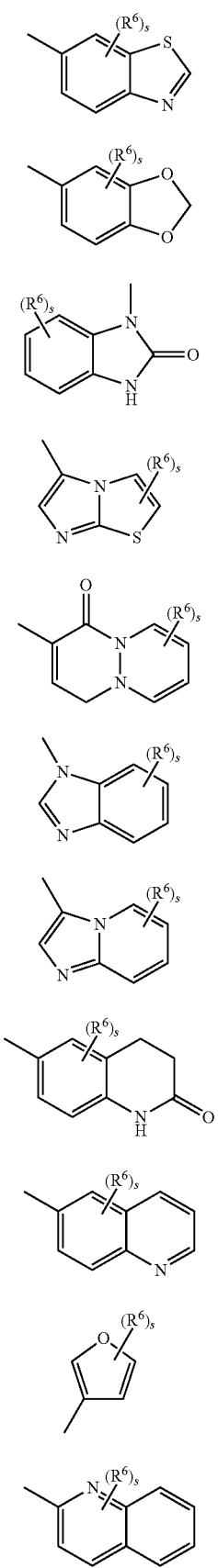
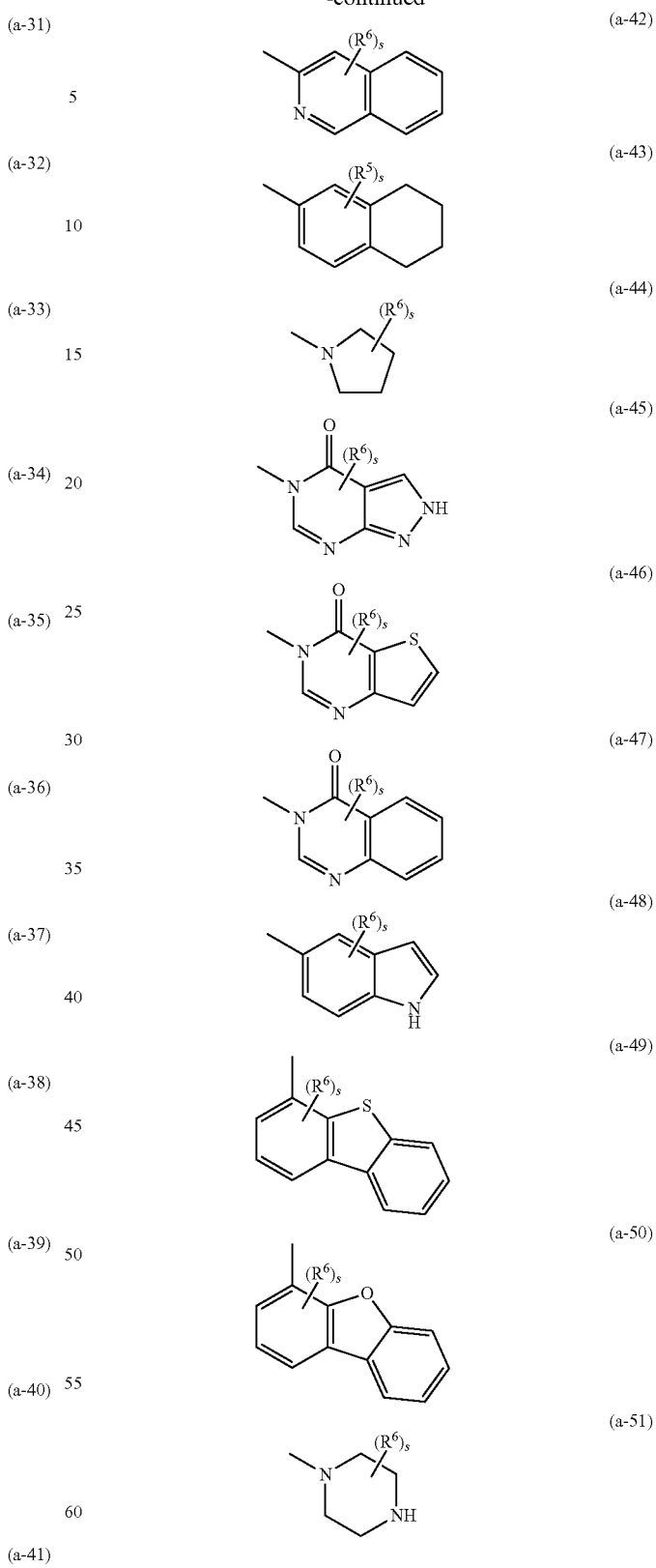
wherein each s is independently 0, 1, 2, 3, 4 or 5, as allowed;
each $R^5$ and $R^6$ are independently hydrogen; halo; hydroxy; amino; nitro; trihalo$C_{1-6}$alkyl; trihalo$C_{1-6}$alkyloxy; $C_{1-6}$alkyl; $C_{1-6}$alkyl substituted with aryl and $C_{3-10}$cycloalkyl; $C_{1-6}$alkyloxy; $C_{1-6}$alkyloxy$C_{1-6}$alkyloxy; $C_{1-6}$alkylcarbonyl; $C_{1-6}$alkyloxycarbonyl; $C_{1-6}$alkylsulfonyl; cyano$C_{1-6}$alkyl; hydroxy$C_{1-6}$alkyl; hydroxy$C_{1-6}$alkyloxy; hydroxy$C_{1-6}$alkyloxy; amino$C_{1-6}$alkyloxy; di(hydroxy$C_{1-6}$alkyl)aminocarbonyl; di(hydroxy$C_{1-6}$alkyl)amino; (aryl)($C_{1-6}$alkyl)amino; di($C_{1-6}$alkyl)amino$C_{1-6}$alkyloxy; di($C_{1-6}$alkyl)amino$C_{1-6}$alkylamino; di($C_{1-6}$alkyl)amino$C_{1-6}$alkylamino$C_{1-6}$alkyl; arylsulfonyl; arylsulfonylamino; aryloxy; aryloxy$C_{1-6}$alkyl; aryl$C_{2-6}$alkenediyl; di($C_{1-6}$alkyl)amino; di($C_{1-6}$alkyl)amino$C_{1-6}$alkyl; di($C_{1-6}$alkyl)amino($C_{1-6}$alkyl)amino; di($C_{1-6}$alkyl)amino($C_{1-6}$alkyl)amino$C_{1-6}$alkyl; di($C_{1-6}$alkyl)amino$C_{1-6}$alkyl($C_{1-6}$alkyl)amino; di($C_{1-6}$alkyl)amino$C_{1-6}$alkyl($C_{1-6}$alkyl)amino$C_{1-6}$alkyl; aminosulfonylamino($C_{1-6}$alkyl)amino; aminosulfonylamino($C_{1-6}$alkyl)amino$C_{1-6}$alkyl; di($C_{1-6}$alkyl)aminosulfonylamino($C_{1-6}$alkyl)amino; di($C_{1-6}$alkyl)aminosulfonylamino($C_{1-6}$alkyl)amino$C_{1-6}$alkyl; cyano; thiopenyl; thiophenyl substituted with di($C_{1-6}$alkyl)amino$C_{1-6}$alkyl($C_{1-6}$)amino$C_{1-6}$alkyl, di($C_{1-6}$alkyl)amino$C_{1-6}$alkyl, $C_{1-6}$alkylpiperazinyl$C_{1-6}$alkyl, hydroxy$C_{1-6}$alkylpiperazinyl$C_{1-6}$alkyl, hydroxy$C_{1-6}$slkyloxy$C_{1-6}$alkylpiperazinyl$C_{1-6}$alkyl, di($C_{1-6}$alkyl)aminosulfonylpiperazinyl$C_{1-6}$alkyl, $C_{1-6}$alkyloxypiperidinyl, $C_{1-6}$alkyloxypiperidinyl$C_{1-6}$alkyl, morpholinyl$C_{1-6}$alkyl, hydroxy$C_{1-6}$alkyl($C_{1-6}$alkyl)amino$C_{1-6}$alkyl, or di(hydroxy$C_{1-6}$alkyl)amino$C_{1-6}$alkyl; furanyl furanyl substituted with hydroxy$C_{1-6}$alkyl; benzofuranyl; imidazolyl; oxazolyl; oxazolyl substituted with aryl and $C_{1-6}$alkyl; $C_{1-6}$alkyltriazolyl; tetrazolyl; pyrrolidinyl; pyrrolyl; piperidinyl$C_{1-6}$alkyloxy;morpholinyl; $C_{1-6}$alkylmorpholinyl; morpholinyl$C_{1-6}$alkyloxy; morpholinyl$C_{1-6}$alkyl; morpholinyl$C_{1-6}$alkylamino; morpholinyl$C_{1-6}$alkylamino$C_{1-6}$alkyl; piperazinyl$C_{1-6}$alkylpiperazinyl; $C_{1-6}$alkylpiperazinyl$C_{1-6}$alkyloxy; piperazinyl$C_{1-6}$alkyl;naphtalenylsulfonylpiperazinyl; naphtalenylsulfonylpiperidinyl; naphtalenylsulfonyl: $C_{1-6}$alkylpiperazinyl$C_{1-6}$alkyl; $C_{1-6}$alkylpiperazinyl-$C_{1-6}$alkylamino; $C_{1-6}$alkylpiperazinyl$C_{1-6}$alkylamino$C_{1-6}$alkyl; $C_{1-6}$alkylpiperazinylsulfonyl; aminosulfonylpiperazinyl$C_{1-6}$alkyloxy; aminosulfonylpiperazinyl; aminosulfonylpiperazinyl$C_{1-6}$alkyl; di($C_{1-6}$alkyl) aminosulfonylpiperazinyl; di($C_{1-6}$alkyl)aminosulfonylpiperazinyl$C_{1-6}$alkyl; hydroxy$C_{1-6}$alkylpiperazinyl; hydroxy$C_{1-6}$alkypiperazinyl$C_{1-6}$alkyl; $C_{1-6}$alkylpiperazinyl; $C_{1-6}$alkyloxypiperidinyl$C_{1-6}$alkyl; piperidinylamino$C_{1-6}$alkylamino; piperidinylamino$C_{1-6}$alkylamino$C_{1-6}$alkyl; ($C_{1-6}$alkylpiperidinyl)(hydroxy$C_{1-6}$alkyl)amino$C_{1-6}$alkylamino; ($C_{1-6}$alkylpiperidinyl)(hydroxy$C_{1-6}$alkyl)amino$C_{1-6}$alkylamino$C_{1-6}$alkyl; hydroxy$C_{1-6}$alkyloxy$C_{1-6}$alkylpiperazinyl; hydroxy-$C_{1-6}$alkyloxy$C_{1-6}$alkylpiperazinyl$C_{1-6}$alkyl; (hydroxy$C_{1-6}$alkyl)($C_{1-6}$alkyl)amino; (hydroxy$C_{1-6}$alkyl)($C_{1-6}$alkyl)amino$C_{1-6}$alkyl; hydroxy$C_{1-6}$alkylamino $C_{1-6}$alkyl; di(hydroxy$C_{1-6}$alkyl)amino$C_{1-6}$alkyl; pyrrolidinyl$C_{1-6}$alkyl; pyrrolidinyl$C_{1-6}$alkyloxy; pyrazolyl; thiopyrazolyl; pyrazolyl substituted with two substituents selected from $C_{1-6}$alkyl or trihalo$C_{1-6}$alkyl; pyridinyl; pyridinyl substituted with $C_{1-6}$alkyloxy, aryloxy or aryl; pyrimidinyl; tetrahydropyrimidinylpiperazinyl; tetrahydropyrimidinylpiperazinyl$C_{1-6}$alkyl; quinolinyl; indolyl; phenyl; phenyl substituted with one, two or three substituents independently selected from halo, amino, nitro, $C_{1-6}$alkyl, $C_{1-6}$alkyloxy, hydroxy$C_{1-4}$alkyl, trifluoromethyl, trifluoromethyloxy, hydroxy $C_{1-4}$alkyloxy, $C_{1-4}$alkylsulfonyl, $C_{1-4}$alkyloxy$C_{1-4}$alkyloxy, $C_{1-4}$alkyloxycarbonyl, amino$C_{1-4}$alkyloxy, di($C_{1-4}$alkyl)amino$C_{1-4}$alkyloxy, di($C_{1-4}$alkyl)amino, di($C_{1-4}$alkyl)aminocarbonyl, di($C_{1-4}$alkyl)amino$C_{1-4}$alkyl, di($C_{1-4}$alkyl)amino$C_{1-4}$alkylamino$C_{1-4}$alkyl, di($C_{1-4}$alkyl)amino($C_{1-4}$alkyl)amino, di($C_{1-4}$alkyl)amino($C_{1-4}$alkyl)amino$C_{1-4}$alkyl, di($C_{1-4}$alkyl)amino$C_{1-4}$alkyl($C_{1-4}$alkyl)amino, di($C_{1-4}$alkyl)amino$C_{1-4}$alkyl($C_{1-4}$alkyl)amino$C_{1-4}$alkyl, aminosulfonylamino($C_{1-4}$alkyl)amino, aminosulfonylamino($C_{1-4}$alkyl)amino$C_{1-4}$alkyl, di($C_{1-4}$alkyl)aminosulfonylamino($C_{1-4}$alkyl)amino, di($C_{1-4}$alkyl)aminosulfonylamino($C_{1-4}$alkyl)amino$C_{1-6}$alkyl, cyano, piperidinyl$C_{1-4}$alkyloxy, pyrrolidinyl$C_{1-4}$alkyloxy, aminosulfonylpiperazinyl, aminosulfonylpiperazinyl$C_{1-4}$alkyl, di($C_{1-4}$alkyl)aminosulfonylpiperazinyl, di($C_{1-4}$alkyl)aminosulfonylpiperazinyl$C_{1-4}$alkyl, hydroxy$C_{1-4}$alkylpiperazinyl, hydroxy$C_{1-4}$alkylpiperazinyl$C_{1-4}$alkyl, $C_{1-4}$alkyloxypiperidinyl, $C_{1-4}$alkyloxypiperidinyl$C_{1-4}$alkyl, hydroxy$C_{1-4}$alkyloxy$C_{1-4}$alkylpiperazinyl, hydroxy $C_{1-4}$alkyloxy$C_{1-4}$alkylpiperazinyl$C_{1-4}$alkyl, (hydroxy$C_{1-4}$alkyl)($C_{1-4}$alkyl)amino, (hydroxy$C_{1-4}$alkyl)($C_{1-4}$alkyl)amino$C_{1-4}$alkyl, di(hydroxy$C_{1-4}$alkyl)amino, di(hydroxy$C_{1-4}$alkyl)amino$C_{1-4}$alkyl, furanyl, furanyl substituted with —CH=CH—CH=CH—, pyrrolidinyl$C_{1-4}$alkyl, pyrrolidinyl$C_{1-4}$alkyloxy, morpholinyl, morpholinyl$C_{1-4}$alkyloxy, morpholinyl$C_{1-4}$alkyl, morpholinyl$C_{1-4}$alkylamino, morpholinyl$C_{1-4}$alkylamino$C_{1-4}$alkyl, piperazinyl, $C_{1-4}$alkylpiperazinyl, $C_{1-4}$alkylpiperazinyl$C_{1-4}$alkyloxy, piperazinyl$C_{1-4}$alkyl, $C_{1-4}$alkylpiperazinyl$C_{1-4}$alkyl, $C_{1-4}$alkylpiperazinyl$C_{1-4}$alkylamino, $C_{1-4}$alkylpiperazinyl$C_{1-4}$alkylamino$C_{1-6}$alkyl, tetrahydropyrimidinylpiperazinyl, tetrahydropyrimidinylpiperazinyl$C_{1-4}$alkyl, piperidinylamino$C_{1-4}$alkylamino, piperidinylamino $C_{1-4}$alkylamino$C_{1-4}$alkyl, ($C_{1-4}$alkylpiperidinyl)(hydroxy$C_{1-4}$alkyl)amino$C_{1-4}$alkylamino, ($C_{1-4}$alkylpiperidinyl$C_{1-4}$alkylamino$C_{1-4}$alkyl, pyridinyl$C_{1-4}$alkyloxy, hydroxy$C_{1-4}$alkylamino, hydroxy$C_{1-4}$alkylamino$C_{1-4}$alkyl, di($C_{1-4}$alkyl)amino$C_{1-4}$alkylamino, aminothiadiazolyl, aminosulfonylpiperazinyl$C_{1-4}$alkyloxy, or thiophenyl$C_{1-4}$alkylamino;

each $R^5$ and $R^6$ can be placed on the nitrogen in replacement of the hydrogen;

wherein aryl in the above is phenyl, or phenyl substituted with one or more substituents that is each independently halo, $C_{1-6}$alkyl, $C_{1-6}$alkyloxy, trifluoromethyl, cyano or hydroxycarbonyl.

2. A compound of formula (I),

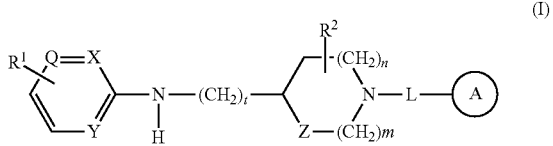

(I)

the N-oxide forms, the pharmaceutically acceptable addition salts and the stereo-chemically isomeric forms thereof, wherein n is 1;
m is 1;
t is 0;
Q is C;
X is N;
Y is N;
Z is —$CH_2$—;

R[1] is —C(O)NR[3]R[4], —C(O)—C$_{1-6}$alkanediylSR[7], —NR[8]C(O)N(OH)R[7], —NR[8]C(O)C$_{1-6}$alkanediylSR[7], or —NR[8]C(O)C=N(OH)R[7] wherein R[3] and R[4] are each independently selected from hydrogen, hydroxy, hydroxyC$_{1-6}$alkyl or aminoC$_{1-6}$alkyl;

R[2] is hydrogen, hydroxy, amino, hydroxyC$_{1-6}$alkyl, C$_{1-6}$alkyl, C$_{1-6}$alkyloxy, arylC$_{1-6}$alkyl, aminocarbonyl, aminoC$_{1-6}$alkyl, C$_{1-6}$alkylaminoC$_{1-6}$alkyl or di(C$_{1-6}$alkyl)aminoC$_{1-6}$alkyl;

-L- is a bivalent radical selected from C$_{1-6}$alkanediyl, carbonyl or sulfonyl;

is a radical that is

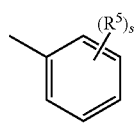 (a-1)

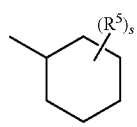 (a-2)

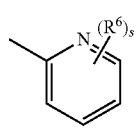 (a-3)

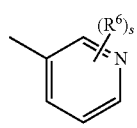 (a-4)

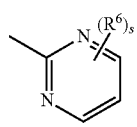 (a-5)

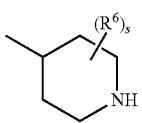 (a-6)

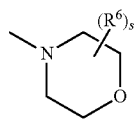 (a-7)

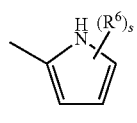 (a-8)

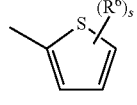 (a-9)

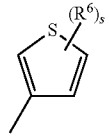 (a-10)

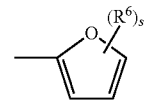 (a-11)

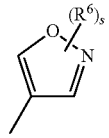 (a-12)

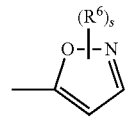 (a-13)

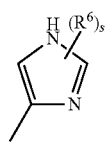 (a-14)

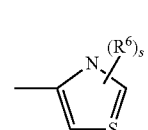 (a-15)

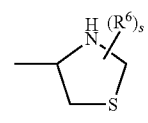 (a-16)

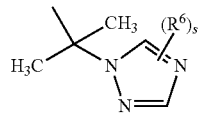 (a-17)

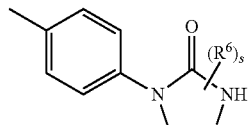 (a-18)

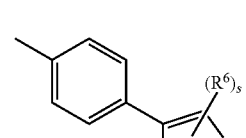 (a-19)

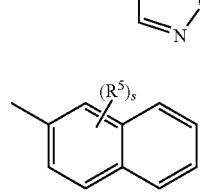 (a-20)

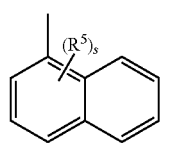 (a-21)
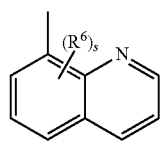 (a-22)
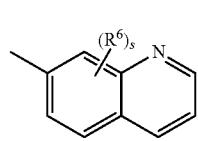 (a-23)
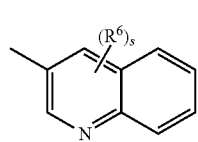 (a-24)
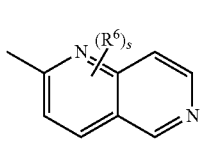 (a-25)
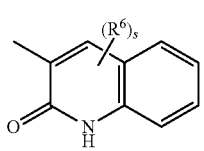 (a-26)
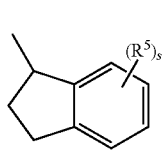 (a-27)
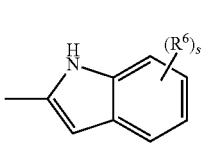 (a-28)
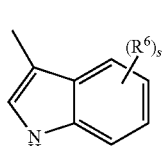 (a-29)
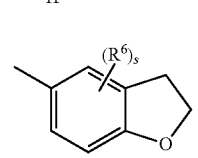 (a-30)
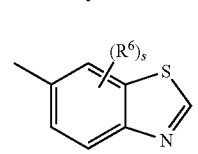 (a-31)
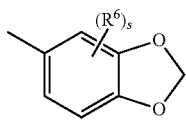 (a-32)
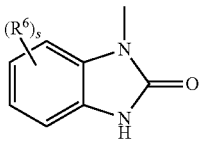 (a-33)
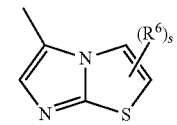 (a-34)
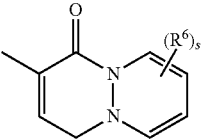 (a-35)
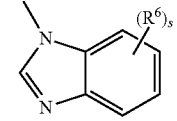 (a-36)
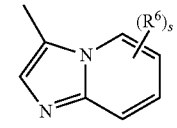 (a-37)
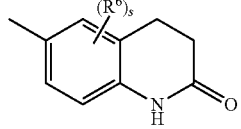 (a-38)
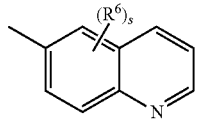 (a-39)
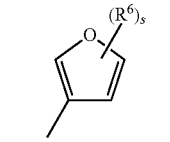 (a-40)
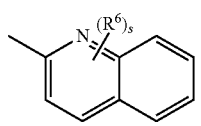 (a-41)
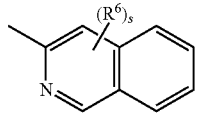 (a-42)

-continued

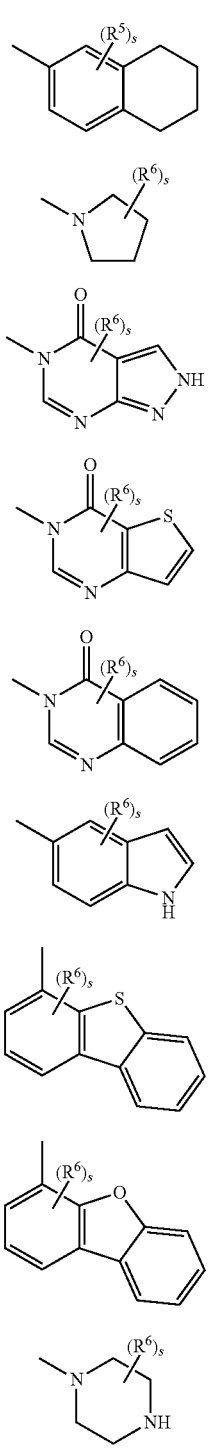

s is 0, 1, 2, 3 or 4, as allowed;

R⁵ is hydrogen; halo; hydroxy; amino; nitro; trihaloC$_{1-6}$alkyl; trihaloC$_{1-6}$alkyloxy; C$_{1-6}$alkyl; C$_{1-6}$alkyloxy; C$_{1-6}$alkylcarbonyl; C$_{1-6}$alkyloxycarbonyl; C$_{1-6}$alkylsulfonyl; hydroxyC$_{1-6}$alkyl; aryloxy; di(C$_{1-6}$alkyl)amino; cyano; thiophenyl; furanyl; furanyl substituted with hydroxyC$_{1-6}$alkyl; benzofuranyl; imidazolyl; oxazolyl; oxazolyl substituted with aryl and C$_{1-6}$alkyl; C$_{1-6}$alkyltriazolyl; tetrazolyl; pyrrolidinyl; pyrrolyl; morpholinyl; C$_{1-6}$alkylmorpholinyl; piperazinyl; C$_{1-6}$alkylpiperazinyl; hydroxyC$_{1-6}$alkylpiperazinyl; C$_{1-6}$alkyloxypiperidinyl; pyrazolyl; pyrazolyl substituted with one or two substituents selected from C$_{1-6}$alkyl or trihaloC$_{1-6}$alkyl; pyridinyl; pyridinyl substituted with C$_{1-6}$alkyloxy, aryloxy or aryl; pyrimidinyl; quinolinyl; indolyl; phenyl; or phenyl substituted with one or two substituents independently selected from halo, C$_{1-6}$alkyl, C$_{1-6}$alkyloxy or trifluoromethyl; and R⁶ is hydrogen; halo; hydroxy; amino; nitro; trihaloC$_{1-6}$alkyl; trihaloC$_{1-6}$alkyloxy; C$_{1-6}$alkyl; C$_{1-6}$alkyloxy; C$_{1-6}$alkylcarbonyl; C$_{1-6}$alkyloxycarbonyl; C$_{1-6}$alkylsulfonyl; hydroxyC$_{1-6}$alkyl; aryloxy; di(C$_{1-6}$alkyl)amino; cyano; pyridinyl; phenyl; or phenyl substituted with one or two substituents independently selected from halo, C$_{1-6}$alkyl, C$_{1-6}$alkyloxy or trifluoromethyl;

wherein aryl in the above is phenyl, or phenyl substituted with one or more substituents that is each independently halo, C$_{1-6}$alkyl, C$_{1-6}$alkyloxy, trifluoromethyl, cyano or hydroxycarbonyl.

3. A compound as claimed in claim 1 wherein R¹ is —C(O)NH(OH); R² is hydrogen; -L- is a bivalent radical that is carbonyl, sulfonyl, or C$_{1-6}$alkanediyl substituted with phenyl;

is a radical that is (a-1), (a-20) or (a-43); s is 0 or 1; and each R⁵ is hydrogen or phenyl.

4. A compound as claimed in claim 1 wherein R¹ is —C(O)NH(OH); R² is hydrogen; -L- is a bivalent radical that is carbonyl or sulfonyl;

is a radical that is (a-1) or (a-20); each s is independently 0 or 1; and each R⁵ is independently selected from hydrogen or phenyl.

5. A compound according to claim 1 that is

Co. No. 5

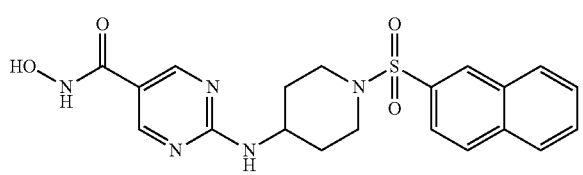

Co. No. 14

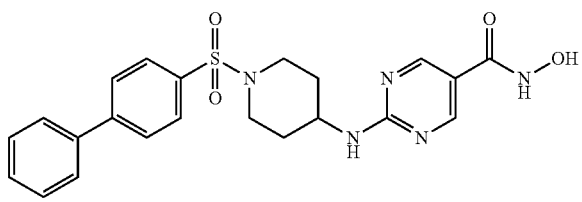

Co. No. 7

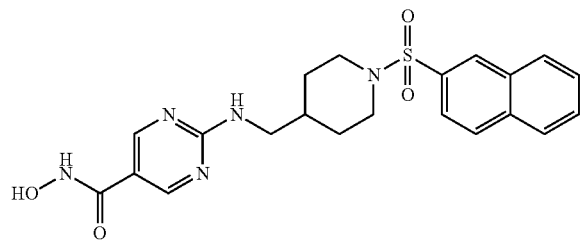

Co. No. 8

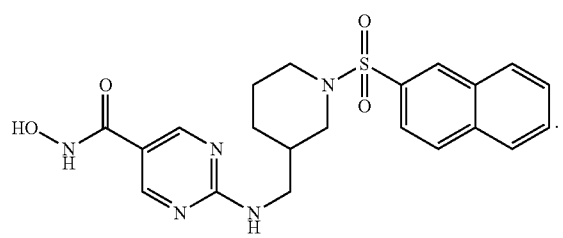

6. A pharmaceutical composition comprising pharmaceutically acceptable carriers and as an active ingredient a therapeutically effective amount of a compound as claimed in claim 1.

7. A process of preparing a pharmaceutical composition as claimed in claim 6 wherein the pharmaceutically acceptable carriers and the compound are intimately mixed.

8. A process for preparing a compound as claimed in claim 1, comprising reacting an intermediate of formula (II)

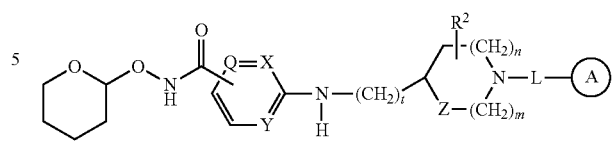

with an appropriate acid, yielding a hydroxamic acid of formula (I-a)

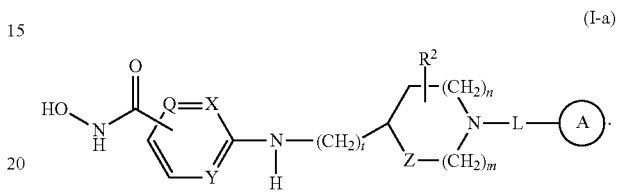

9. The method of claim 8 wherein the acid is trifluoroacetic acid.

10. A method of detecting or identifying a histone deactylase (HDAC) in a biological sample comprising detecting or measuring the formation of a complex between a labelled compound as defined in claim 1 and a HDAC.

11. The compound of claim 1 wherein n is 1 and m is 1.

* * * * *